US005650322A

United States Patent [19]

Clarkson et al.

[11] Patent Number: 5,650,322

[45] Date of Patent: Jul. 22, 1997

[54] METHODS FOR STONEWASHING FABRICS USING ENDOGLUCANASES

[75] Inventors: Kathleen A. Clarkson, San Francisco; Edmund Larenas, Moss Beach; Geoffrey Weiss; Benjamin S. Bower, both of San Francisco, all of Calif.

[73] Assignee: Genencor International, Inc., South San Francisco, Calif.

[21] Appl. No.: 954,113

[22] Filed: Sep. 30, 1992

Related U.S. Application Data

[63] Continuation-in-part of Ser. No. 677,385, Mar. 19, 1991, abandoned, and a continuation-in-part of Ser. No. 678,865, Mar. 29, 1991, abandoned, and a continuation-in-part of Ser. No. 770,049, Oct. 4, 1991, abandoned, each is a continuation-in-part of Ser. No.593,919, Oct. 5, 1990, abandoned.

[51] Int. Cl.$^6$ .......................... D06M 16/00; C12N 9/42; C11D 9/40
[52] U.S. Cl. .......................... 435/263; 435/209; 510/392
[58] Field of Search .......................... 435/172.3, 69.1, 435/209, 254, 320.1, 263; 252/816, 174.12

[56] References Cited

U.S. PATENT DOCUMENTS

| | | | |
|---|---|---|---|
| 4,275,163 | 6/1981 | Gallo | 435/209 |
| 4,435,307 | 3/1984 | Barbesgaard et al. | 252/174.12 |
| 4,472,504 | 9/1984 | Gallo | 435/209 |
| 4,479,881 | 10/1984 | Tai | 252/8.8 |
| 4,487,831 | 12/1984 | Day et al. | 435/99 |
| 4,648,979 | 3/1987 | Parslow et al. | 252/8.8 |
| 4,661,289 | 4/1987 | Parslow et al. | 252/547 |
| 4,725,544 | 2/1988 | Tan et al. | 435/200 |
| 4,738,682 | 4/1988 | Boegh et al. | 8/401 |
| 4,762,788 | 8/1988 | Warzywoda et al. | 435/209 |
| 4,797,361 | 1/1989 | Montenecourt | 435/198 |
| 4,822,516 | 4/1989 | Suzuki et al. | 252/174.12 |
| 4,832,864 | 5/1989 | Olson | 252/174.12 |
| 4,894,338 | 1/1990 | Knowles et al. | 435/172.3 |
| 4,912,056 | 3/1990 | Olson | 435/263 |
| 4,945,053 | 7/1990 | Ito et al. | 435/209 |
| 4,952,505 | 8/1990 | Cho | 435/209 |
| 4,978,470 | 12/1990 | Suzuki et al. | 252/174.12 |
| 5,006,126 | 4/1991 | Olson et al. | 8/401 |
| 5,045,464 | 9/1991 | Ito et al. | 435/209 |
| 5,120,463 | 6/1992 | Bjork et al. | 252/174.12 |
| 5,122,159 | 6/1992 | Olson et al. | 8/401 |

FOREIGN PATENT DOCUMENTS

| | | |
|---|---|---|
| 0120528 | 10/1984 | European Pat. Off. . |
| 0137280 | 4/1985 | European Pat. Off. . |
| 0173397 | 3/1986 | European Pat. Off. . |
| 0220016 | 4/1987 | European Pat. Off. . |
| 0244234 | 11/1987 | European Pat. Off. . |
| 0271004 | 6/1988 | European Pat. Off. . |
| 2148278 | 3/1972 | Germany . |
| 58-36217 | 3/1983 | Japan . |
| 58-54082 | 3/1983 | Japan . |
| 64-40681 | 2/1989 | Japan . |
| 1368599 | 10/1974 | United Kingdom . |
| 2095275 | 9/1982 | United Kingdom . |
| 2094826 | 9/1982 | United Kingdom . |
| 85/04672 | 10/1985 | WIPO . |
| 89/09259 | 10/1989 | WIPO . |
| 9002790 | 3/1990 | WIPO . |
| 91/05841 | 5/1991 | WIPO . |
| 9110732 | 7/1991 | WIPO . |
| 91/13136 | 9/1991 | WIPO . |
| 91/17243 | 11/1991 | WIPO . |

OTHER PUBLICATIONS

JP 62062898 A published Mar. 19, 1987, Abstract Only.
Bhikhabhai et al. (1984) FEBS vol. 167(2):301–308.
S. Aho, "Structural and functional analysis of *Trichoderma reesei* endoglucanase I expressed in yeast *Saccharomyces cerevisiae*", *FEBS Letters*, 291:45–49 (1991).
Berg et al., "Enzyme–Gold Affinity Labelling of Cellulose", *Journal of Electron Microsc. Tech.*8:371–379 (1988) [Abstract].
Bhat et al., "The Endo–(1→4)–β–D–Glucanase System of *Pencillium pinophilum* Cellulase: Isolation, Purification, and Characterization of Five Major Endoglucanase Components", *Carbohydrate Research*, 190:279–297 (1989).
Brown et al., "Microbial Enzymes and Lignocellulose Utilization," *Genetic Control of Environmetnal Pollutants*, Omen Editor, Plenum Publishing Corp., pp. 239–265 (1984).
Chen et al., "Nucleotide Sequence and Deduced Primary Structure of Cellobiohydrolase II from *Trichoderma reesei*", *Biotechnology*, vol. 5, pp.274–278 (1987).
Corrick et al., "The Nucleotide Sequence of the amdS Gene of *Aspergillus nidulans* and the Molecular Characterization of 5' Mutations", *Gene* 53:63–71 (1987).
Coughlan et al., "Comparative Biochemistry of Fungal and Bacterial Cellulolytic Enzyme Systems," *Biochemistry and Genetics of Cellulose Degradation*, Aubert et al., Editors, pp. 11–30 (1988).
Hakansson et al., "Purification and Characterization of a Low Molecular Weight 1,4–β–Glucan Glucanohydrolase from the Cellulolytic Fungus *Trichoderma viride* QM 9414", *Biochimica et Biophysica Acta*, 524:385–392 (1978).
Hakansson, Dissertation, Faculty of Science, Uppsala University, pp. 6–23 (1981).
Harkki et al., "Genetic engineering of Trichoderma to produce strains with novel cellulase profiles", *Enzyme Microb. Technol.*, 13:227–233 (1991).
Hayashida et al., "Production and Purification of Thermostable Cellulases from *Humicola insolens* YH–8," *Agri. Biol. Chem.*, 44(8):1721–1728 (1980).

(List continued on next page.)

*Primary Examiner*—Mindy Fleisher
*Assistant Examiner*—James Ketter
*Attorney, Agent, or Firm*—Burns, Doane, Swecker & Mathis, L.L.P.

[57] ABSTRACT

Disclosed are improved aqueous processes and compositions for obtaining a "stonewashed", look in colored fabric while reducing the amount of redeposition of colorant onto the fabric, as well as the fabrics produced from these methods. In particular, the disclosed methods as directed to contacting fabrics with fungal cellulase composition which is substantially free of CBH type components. Fabrics so treated show reduced redeposition of colorant.

8 Claims, 8 Drawing Sheets

OTHER PUBLICATIONS

Hayashida et al., "The Role of Carbohydrate Moiety on Thermostability of Cellulases from *Humicola insolens* YH–8" *Agri. Biol. Chem.*, 44(3):481–487 (1980).

Hayashida et al., "Cellulases of *Humicola insolens* and *Humicola grisea*", *Methods in Enzymology*, 160:323–332 (1988).

Innovations, "Back Staining, A Problem? Not Anymore!", (1991) 2 pages.

*International Textile Bulletin, Dyeing/Printing/Finishing,* "Softening and Polishing of Cotton Fabrics by Cellulase Treatment", 2nd Quarter, pp. 5–8 (1990).

JTN, "Weight Loss Treatment to Soften the Touch of Cotton Fabric;" p. 64 (Dec. 1988).

Kenkyushitsu et al., "The Improvement of Cellulose Fibers by Means of Cellulase".

Knowles et al., "The use of gene technology in the development of novel cellulolytic organisms—*Trichoderma reesei* cellulase and cellulobiohydrolase gene cloning and expression; a review", *Recent Adv. Biotechnol. Appl. Biol.*, pp. 139–142 (1988) [Abstract].

Knowles et al., "The use of gene technology to investigate fungal cellulolytic enzymes *Trichoderma reesei* cellulase complex gene cloning and expression in *Saccharomyces cerevisiae*", *FEMS Symp.* 43;153–169 (1988) [Abstract].

Kochavi et al., "Optimizing Processing Conditions in Enzymatic Stonewashing", *Amer. Dyestuff Reporter*, Sep. 1990, pp. 24, 26 and 28.

Kubicek–Pranz et al., "Transformation of *Trichoderma reesei* with cellobiohydrolase II gene as a means for obtaining strains with increased cellulase production and specific activity", *Journal of Biotechnology*, 20:83–94 (1991).

Kubicek–Pranz et al., "Characterization of Commercial *Trichoderma–reesei* Cellulase Preparations by Denaturing Electrophoresis SDS–PAE and Immunostaining Using Monoclonal Antibodies", *Biotechnol. Appl. Biochem.*, 14:317–323 (1991) [Abstract].

Luderer et al., "A Re–appraisal of Multiplicity of Endoglucanase I from *Trichoderma reesei* Using Monoclonal Antibodies and Plasma Desorption Mass Spectrometry", *Biochim. Biophys. Acta*, 1076:427–434 (1991) [Abstract].

Miller et al., "Direct and Indirect Gene Replacements in *Aspergillus nidulans*", *Mol. and Cell. Biol.*, vol. 5(7), pp. 1714–1721 (1985).

Murphy–Holland et al., "Secretion activity and stability of deglycosylated cellulase of *Trichoderma reesei* gene cloning", *Abstr. Annu. Meet. Am. Soc. Microbiol.*, 85 Meet., vol. 193 (1985) [abstract].

Ohishi et al., "Reformation of Cotton Fabric by Cellulase;" pp. 1–12.

Penttilä et al., "Expression of Two *Trichoderma reesei* Endoglucanases in the Yeast *Saccharomyces cerevisiae*", *Yeast*, 3:175–185 (1987).

Penttilä et al., "Homology between cellulase genes of *Trichoderma reesei*: complete nucleotide sequence of the endoglucanase I gene", *Gene*, vol. 45, pp. 253–263 (1986).

Reinikainen et al., "How Do *Trichoderma reesei* cellobiohydrolase bind to and degrade cellulose", *Abstr. Pap. Am. Chem. Soc.*, 202 Meet. Pt. 1, (1991) [Abstract].

Saloheimo et al., "EGIII a new endoglucanase from *Trichoderma reesei*: the characterization of both gene and enzyme", *Gene*, 63:11–22 (1988).

Sambrook et al., *Molecular Cloning A Laboratory Manual*, 2nd Ed., Cold Spring Harbor Laboratory Press, pp. 1.53–1.73 (1989).

Schulein, "Cellulases of *Trichoderma reesei*", *Methods in Enzymology*, 160:234–242 (1988).

Sheir–Neiss et al., "Characterization of the Secreted Celluloses of *Trichoderma reesei* Wild Type and Mutants During Controlled Fermentations", *Appl. Microbiol. Biotechnol.*, 20:46–53 (1984).

Shoemaker et al., "Molecular Cloning of Exo–cellobiohydrolase I Derived from *Trichoderma reesei* Strain L27," *Biotechnology*, 1;691 (1983).

Shoemaker et al., "Characterization and Properties of Cellulases Purified from *Trichoderma reesei* Strain L27," *Biotechnology*, pp. 687–690 (1983).

Smith et al., "Sequence of the Cloned pyr4 Gene of *Trichoderma reesei* and its use as a Homologous Selectable Marker for Transformation", *Curr. Genetics*, 19:27–33 (1991).

Teeri, "The Cellulolytic Enzyme System of *Trichoderma reesei*", *Publications* 38, pp. 13, 17–20 of 1–52 + Appendices (1987).

Teeri et al., "Engineering Trichoderma and its cellulases *Trichoderma reesei* cellulase and cellobiohydrolase gene cloning and expression: potential strain improvement and enzyme engineering" *Trichoderma reesei Cellulases* pp. 156–167 (1990) [abstract].

Ulker et al., "Characterization of an Unglycosylated Low Molecular Weight 1,4–B–glucan–glucanohydrolase of *Trichoderma reesei*", *FEMS Microbiology Letters*, 69:215–219 (1990).

Uusitalo et al., "Enzyme Production by recombinant *Trichoderma reesei* strains", *Journal of Biotechnology* 17:35–49 (1991).

van Arsdell, "Cloning, Characterization and Expression in *Saccharomyces cervisiae* of Endoglucanase I from *Trichoderma reesei*", *Bio/Technology* 5:60–64 (1987).

Voragen et al., "Cellulases of a Mutant Strain of *Trichoderma viride* QM 9414", *Methods in Enzymology* 160:243–251 (1988).

Wilson et al., "Sequence of the p*Aspergillus niger* pyrG Gene", *Nucl. Acids Res.* 16:2339 (1988).

Wilson et al., "Expression Vector pT7: TKII for the Synthesis of Authentic Biologically Active RNA Encoding Vaccinia Virus Thymidine Kinase", *Gene* (1984) 77:69–78.

Wood, "Properties of Cellulolytic Enzyme Systems," *Biochem. Soc. Trans.*, 13:407–410 (1985).

Wood et al., "Methods for Measuring Cellulase Activities" *Methods in Enzymology* 160:87–112 (1988).

Wood et al., "Aerobic and Anaerobic Fungal Cellulases, With Special Reference to Their Mode of Attack on Crystalline Cellulose", *Biochemistry and Genetics of Cellulose Degradation*, pp. 31–52 (1988).

Wood et al., "The Mechanism of Fungal Cellulose Action", *Biochem J.* 260:37–43 (1989).

Yamagishi, "Reforming of Cellulosic Fiber With Cellulose", *The Shizuoka Prefectural Hamamatsu Textile Industrial Research Institute Report* 24:54–61 (1986).

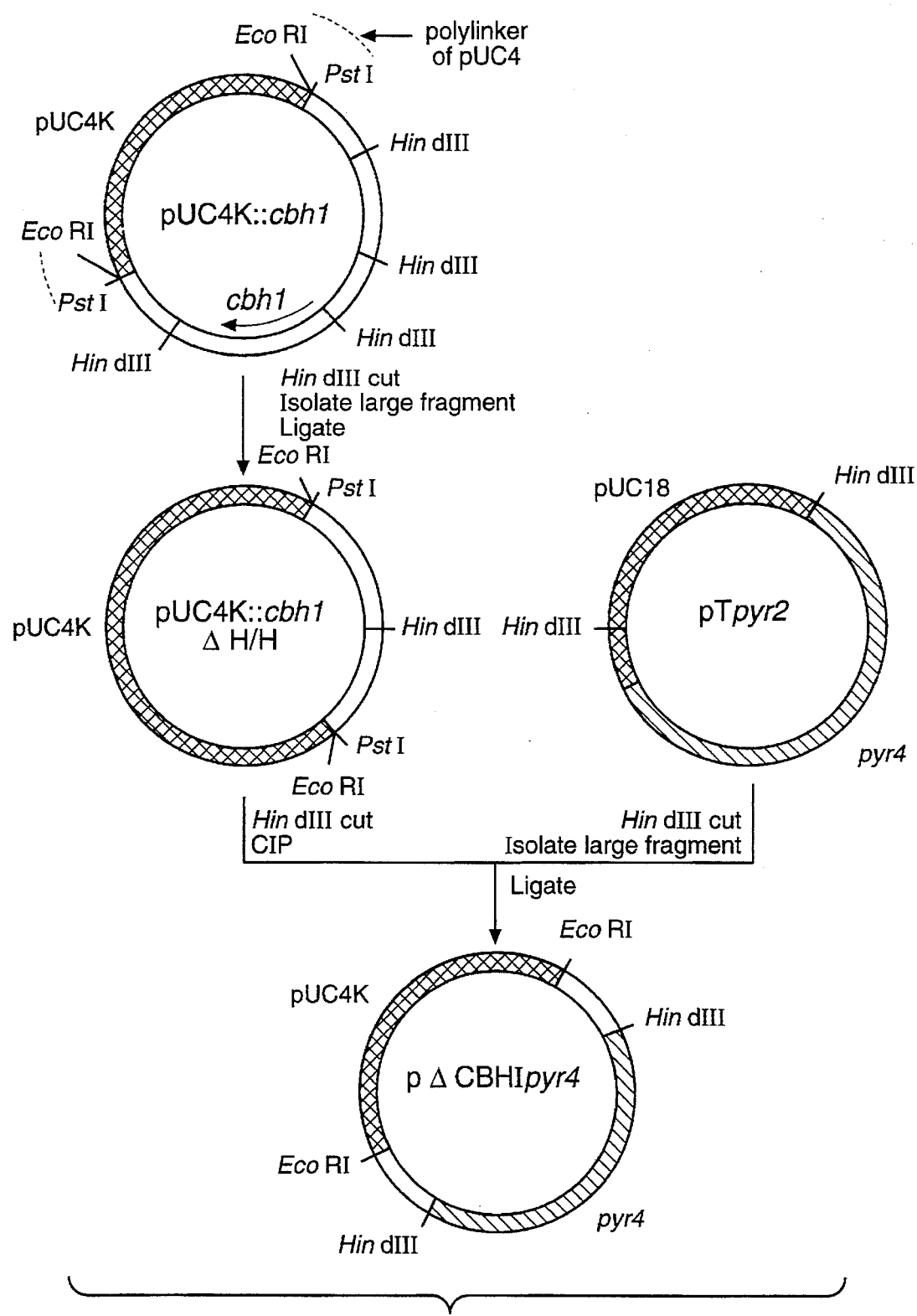
FIG._1

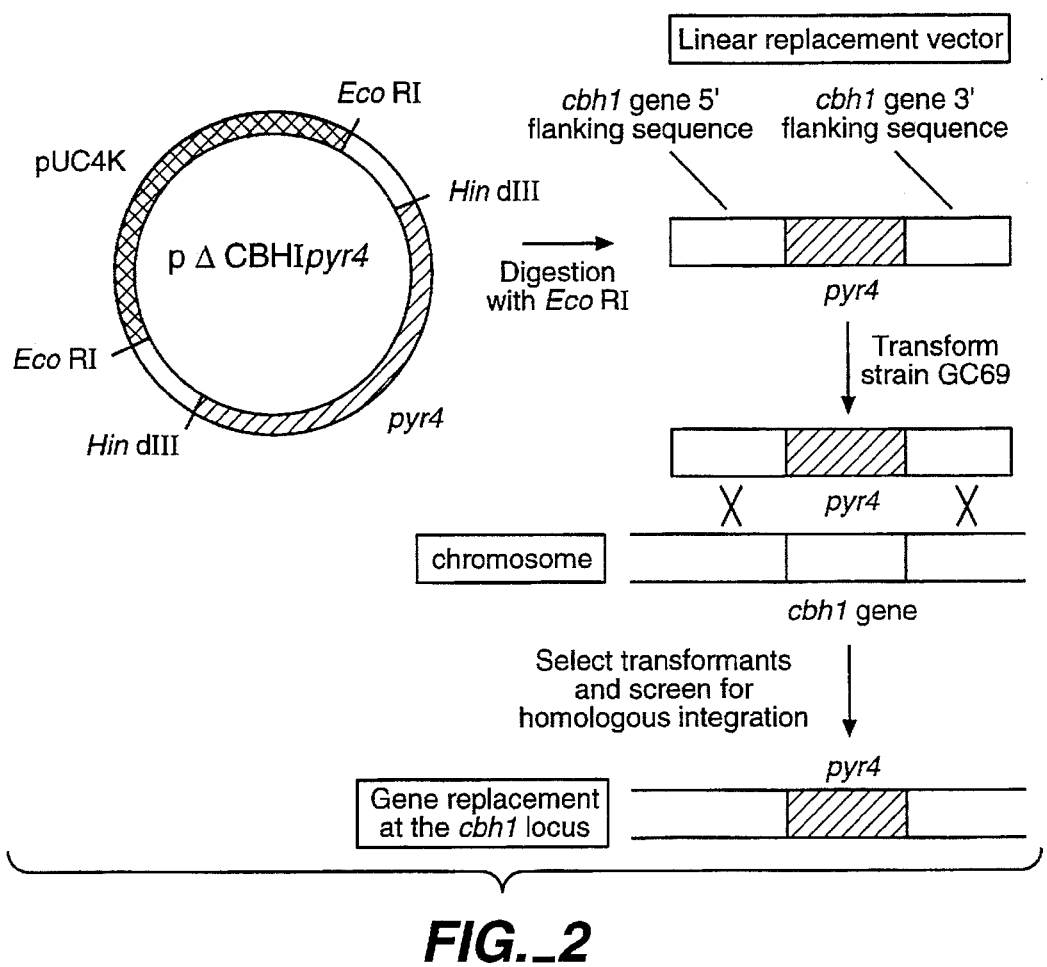
FIG._2
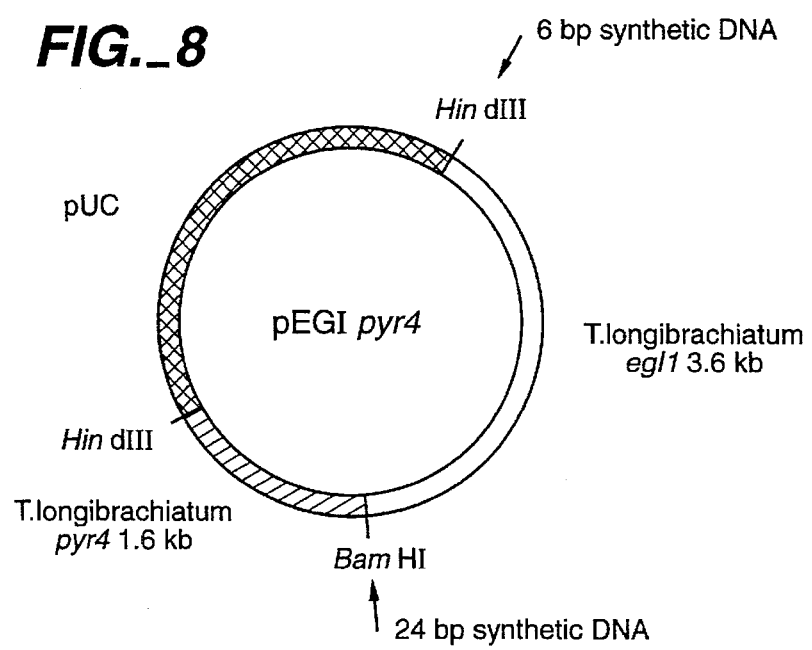
FIG._8

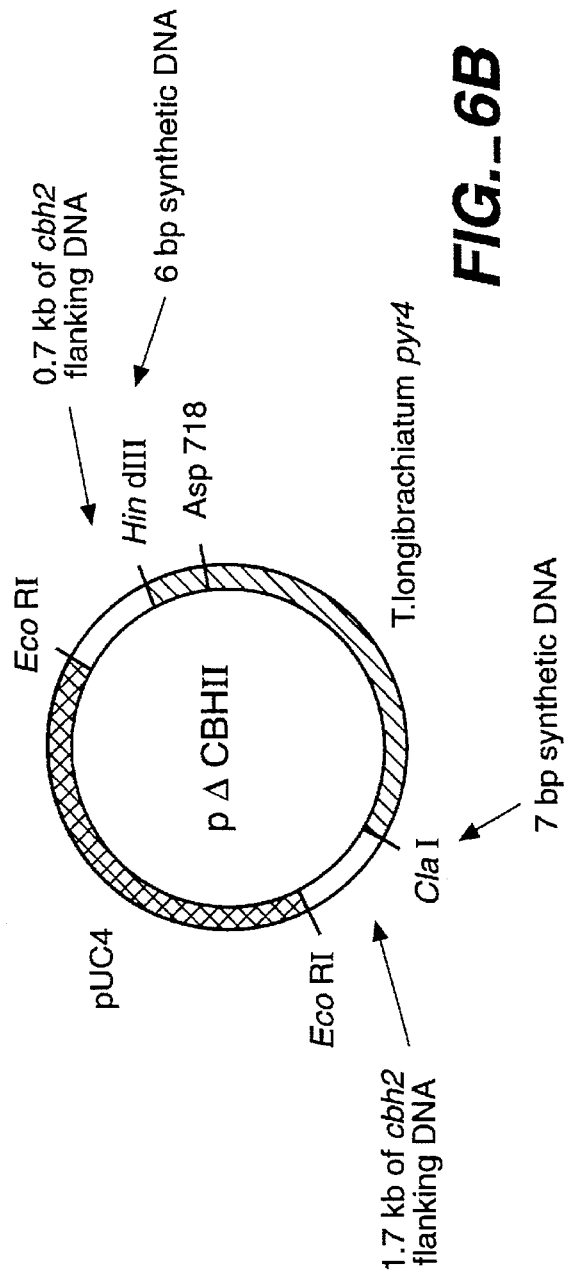
FIG._6A
FIG._6B

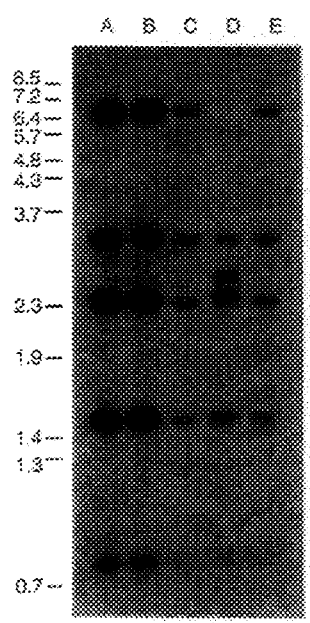
FIG._3
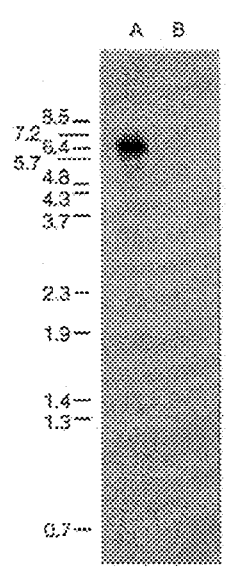
FIG._4
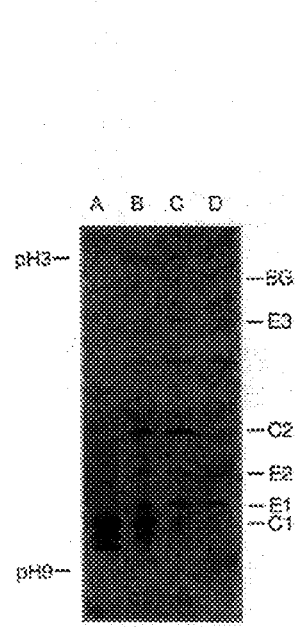
FIG._5
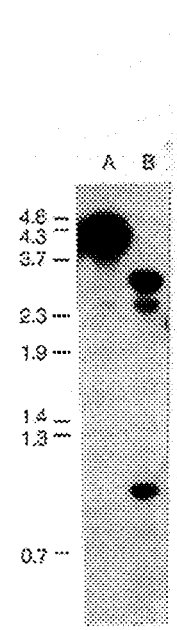
FIG._7

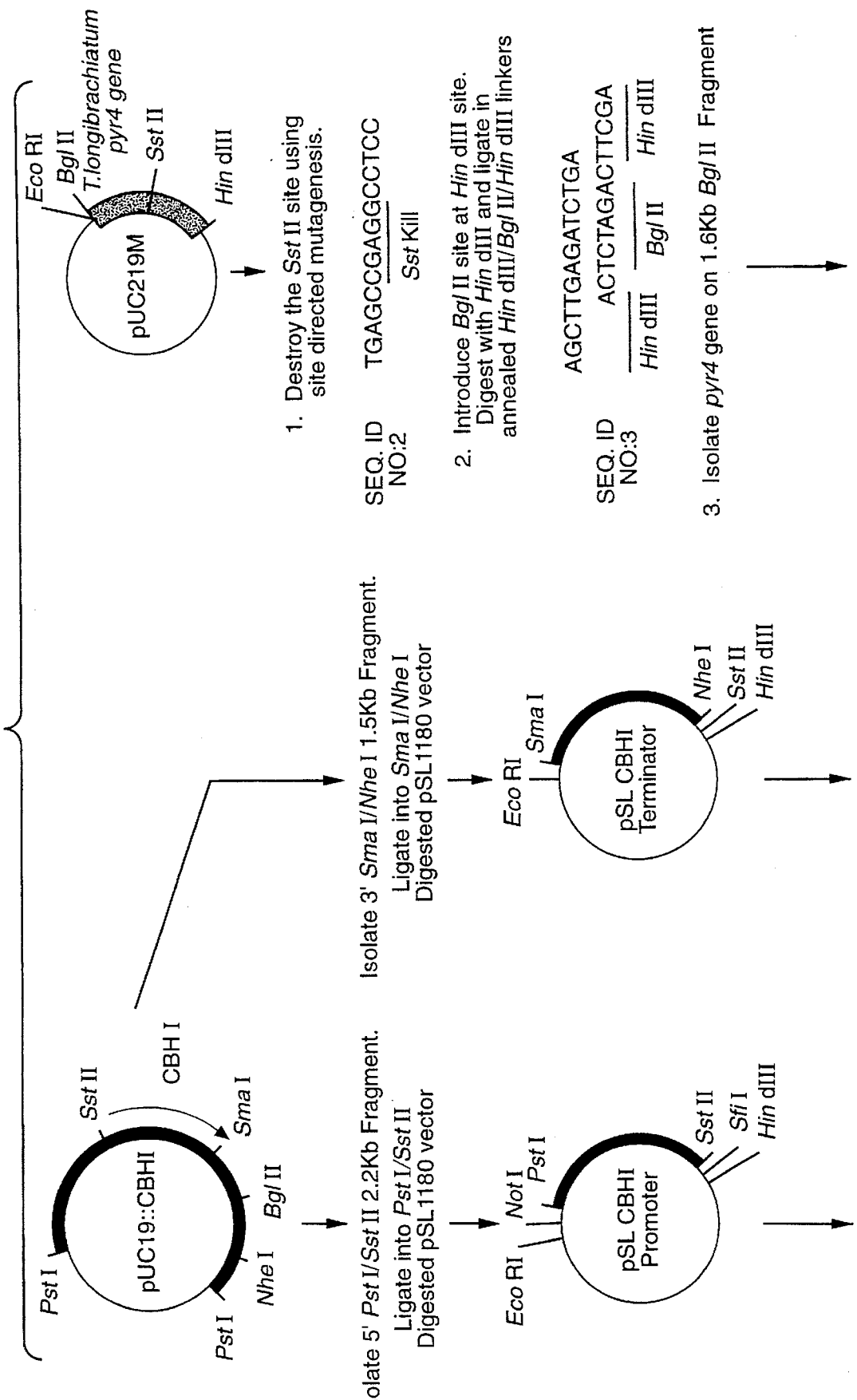

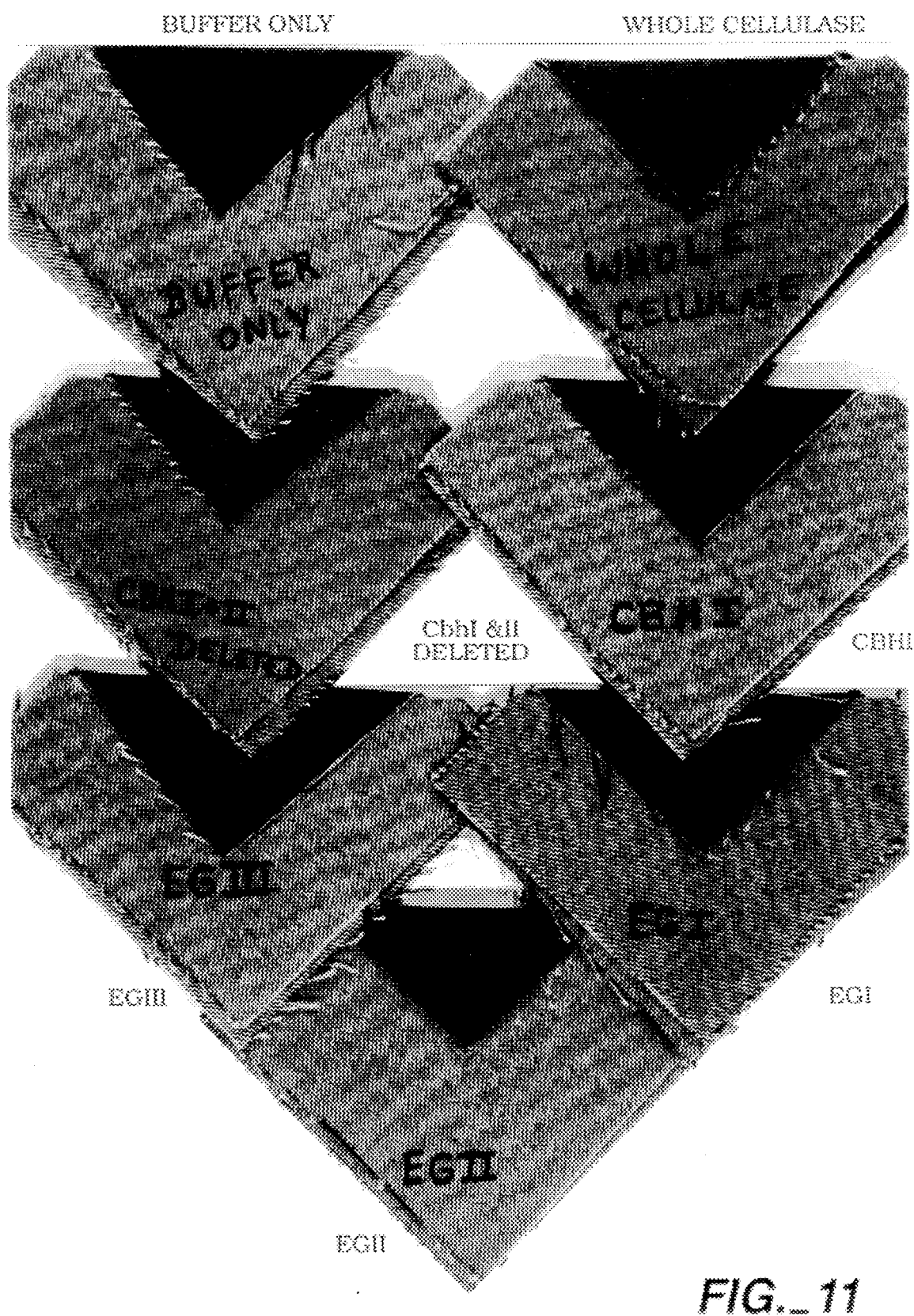
FIG._11

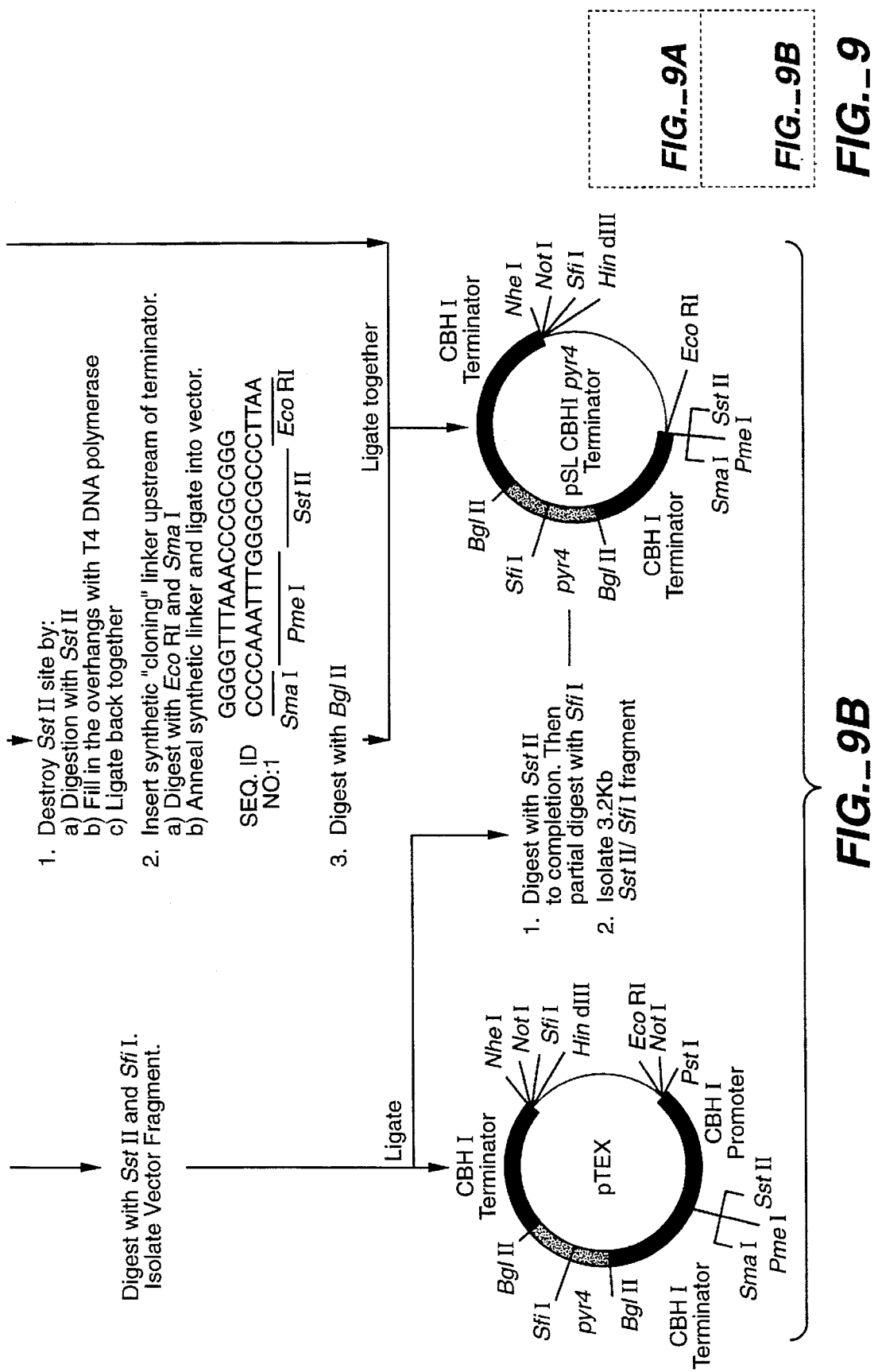
FIG._9B

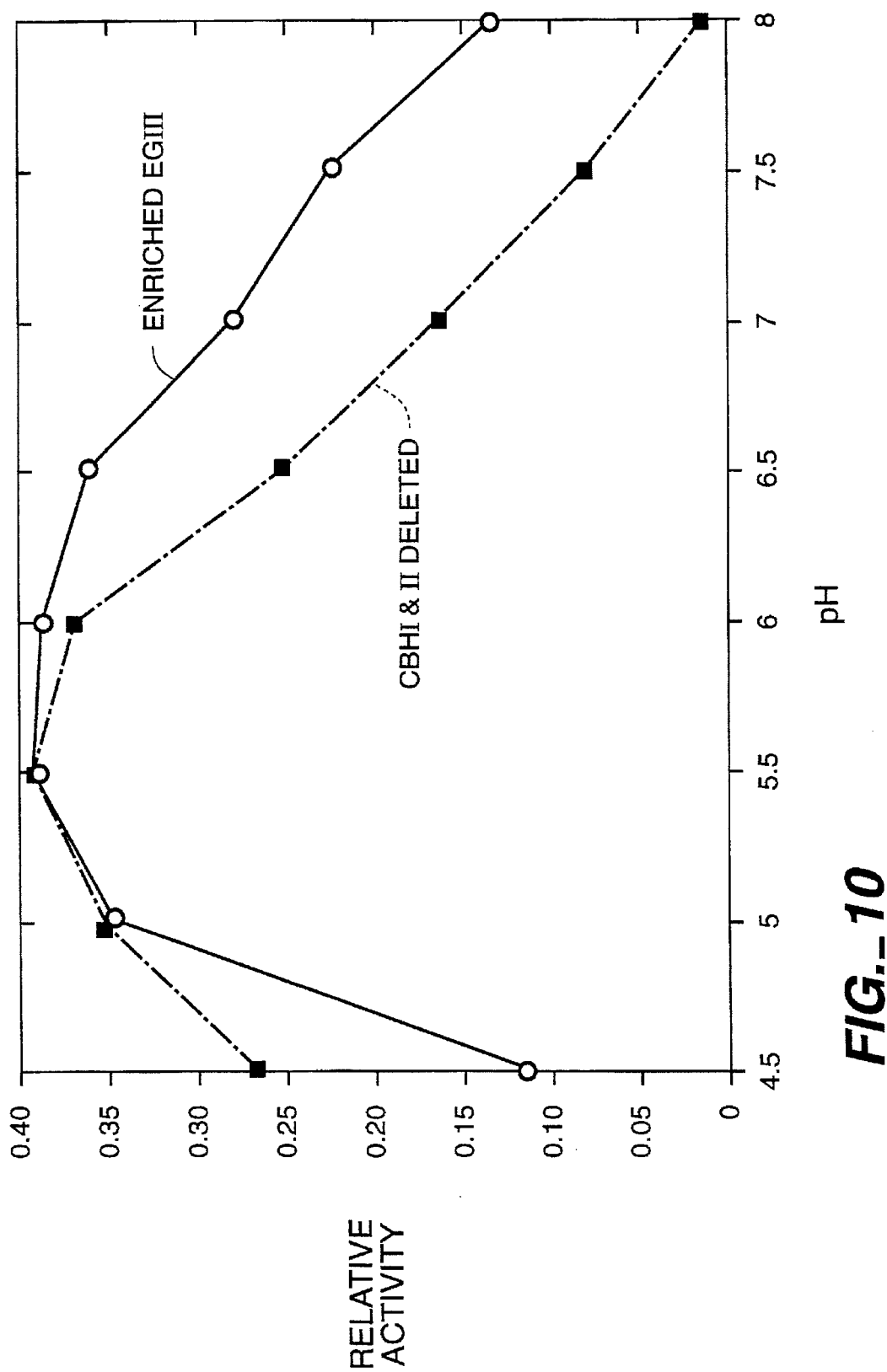
FIG._10

METHODS FOR STONEWASHING FABRICS USING ENDOGLUCANASES

CROSS-REFERENCE TO RELATED APPLICATIONS

This application is a continuation-in-part of U.S. Ser. No. 07/677,385 filed Mar. 29, 1991, now abandoned; U.S. Ser. No. 07/678,865 filed Mar. 29, 1991, now abandoned, and U.S. Ser. No. 07/770,049 filed Oct. 4, 1991, now abandoned, each of which are continuations-in-part of U.S. Ser. No. 07/593,919 filed Oct. 5, 1990 now abandoned and all of which are incorporated herein by reference in their entirety.

BACKGROUND OF THE INVENTION

1. Field of the Invention

The present invention is directed to compositions and methods for achieving a stonewashed appearance in fabric while reducing or preventing the backstaining of colorant onto the fabric as well as to the fabric and clothing produced from these methods. In particular, the improved methods of the present invention are directed to contacting the fabrics with an aqueous solution containing a fungal cellulase composition which comprises endoglucanase type components substantially free of CBH type components. When the fabric is treated with such solutions, the amount of backstaining of colorant onto the fabric during the stonewashing of the fabric is reduced.

2. State of the Art

Clothing made from cellulosic fabrics, such as cotton denim, is stiff in texture due to the presence of sizing compositions used to ease manufacturing, handling and assembling of clothing items and typically has a fresh dark dyed appearance. One desirable characteristic of indigo-dyed denim cloth is the alteration of dyed threads with white threads, which gives denim a white on blue appearance.

After a period of extended wear and laundering, the clothing items, particularly denim, can develop in the clothing panels and on seams, localized areas of variation in the form of a lightening, in the depth or density of color. In addition, a general fading of the clothes, some pucker in seams and some wrinkling in the fabric panels can often appear. Additionally, after laundering, sizing is substantially removed from the fabric resulting in a softer feel. In recent years such a distressed or "stonewashed" look, particularly in denim clothing, has become very desirable to a substantial proportion of the public.

The previous methods for producing the distressed look involved stonewashing of a clothing item or items in a large tub with pumice stones having a particle size of about 1 to 10 inches and with smaller pumice particles generated by the abrasive nature of the process. Typically the clothing item is tumbled with the pumice while wet for a sufficient period such that the pumice abrades the fabric to produce in the fabric panels, localized abraded areas of lighter color and similar lightened areas in the seams. Additionally the pumice softens the fabric and produces a fuzzy surface similar to that produced by the extended wear and laundering of the fabric. This method produced the desired white on blue contrast described above.

The use of the pumice stones has several disadvantages, including overload damage to the machine motors, mechanical damage to transport mechanisms and washing drums, environmental waste problems from the grit produced and high labor costs associated with the manual removal of the stones from the pockets of the garments.

In view of the problems associated with pumice stones in stonewashing, whole cellulase solutions are used as a replacement for the pumice stones under agitating and cascading conditions, i.e., in a rotary drum washing machine, to impart a "stonewashed" appearance to the denim (U.S. Pat. No. 4,832,864).

A problem with the use of whole cellulase compositions from Trichoderma sp. microorganisms and other fungal sources is the incomplete removal of colorant caused by redeposition or backstaining of some of the dye back onto the cloth during the stonewashing process. In the case of denim fabric, this causes recoloration of the blue threads and blue coloration of the white threads, resulting in less contrast between the blue and white threads and abrasion points (i.e., a blue on blue look rather than the preferred white on blue). See, American Dyestuff Reporter, Sept. 1990, pp. 24–28. This redeposition is objectionable to some users.

Trichoderma cellulases, even though they result in backstaining are preferred because of their higher activity on denim material. In addition, cellulases with a higher degree of purity may be beneficial in the present invention. High specific activity or a high level of purity results in a higher degree of abrasion in a significantly shorter processing time and therefor, is preferable to the denim processors.

Attempts to reduce the amount of redeposition of dye included the addition of extra chemicals or enzymes, such as surfactants, proteases or other agents, into the cellulase wash to help disperse the loosened dye. In addition, processors have used less active whole cellulase, along with extra washings. However, this results in additional chemical costs and longer processing times. Another method includes the use of a mild bleach agent or stain removing agent in the process. This method affects the garment's final shade and increases the processing time. Finally the use of enzymes and stones together leave the processor with all the problems caused by the use of the stones alone.

Accordingly, it would be desirable to find a method to prevent redeposition of colorant during stonewashing of clothing with cellulases.

SUMMARY OF THE INVENTION

The present invention is directed to the discovery that the redeposition of colorant onto fabric during the stonewashing process can be reduced by employing a fungal cellulase composition which is substantially free of CBH type components. It has been found that stonewashing with EG type components result in the reduced redeposition of colorant onto fabric resulting in abrasion points that are more distinct. For example, with indigo dyed denim improved contrast between white and blue yarns is obtained giving a superior stonewashed look.

In view of the above, in one of its method aspects, the present invention is directed to an improved method for reducing colorant redeposition during the stonewashing of colored fabrics which method comprises contacting the fabric with an effective amount of a fungal cellulase solution derived from a redepositing whole fungal cellulase composition under conditions sufficient to impart a stone-washed appearance to the fabric wherein said cellulase solution is substantially free of CBH type components. In a preferred embodiment, the fungal cellulase composition employed herein comprises substantially pure EG I, EG II, and/or substantially pure EG III components. In still another preferred embodiment, the fungal cellulase composition comprises at least about 40 weight percent and preferably at least about 70 weight percent of EG type components based on the total weight of protein in the cellulase composition.

Cotton-containing fabrics or clothing treated by the methods of this invention unexpectedly possess both enhancement of a stonewashed appearance and a reduced redeposition of colorant as compared to the fabric treated with whole cellulase.

In its composition aspects, the present invention is directed to a cotton-containing fabric or clothing treated in the methods of this invention as defined above.

BRIEF DESCRIPTION OF THE DRAWINGS

FIG. 1 is an outline of the construction of pΔCBHIpyr4.

FIG. 2 illustrates deletion of the *T. longibrachiatum* gene by integration of the larger EcoRI fragment from pΔCBHIpyr4 at the cbh1 locus on one of the *T. longibrachiatum* chromosomes.

FIG. 3 is an autoradiograph of DNA from *T. longibrachiatum* strain GC69 transformed with EcoRI digested pΔCBHIpyr4 after Southern blot analysis using a $^{32}P$ labelled pΔCBHIpyr4 as the probe. The sizes of molecular weight markers are shown in kilobase pairs to the left of the Figure.

FIG. 4 is an autoradiograph of DNA from a *T. longibrachiatum* strain GC69 transformed with EcoRI digested pΔCBHIpyr4 using a $^{32}P$ labelled pIntCBHI as the probe. The sizes of molecular weight markers are shown in kilobase pairs to the left of the Figure.

FIG. 5 is an isoelectric focusing gel displaying the proteins secreted by the wild type and by transformed strains of *T. longibrachiatum*. Specifically, in FIG. 5, Lane A of the isoelectric focusing gel employs partially purified CBHI from *T. longibrachiatum*; Lane B employs a wild type *T. longibrachiatum*: Lane C employs protein from a *T. longibrachiatum* strain with the cbh1 gene deleted; and Lane D employs protein from a *T. longibrachiatum* strain with the cbh1 and cbh2 genes deleted. In FIG. 5, the right hand side of the figure is marked to indicate the location of the single proteins found in one or more of the secreted proteins. Specifically, BG refers to the β-glucosidase, E1 refers to endoglucanase I, E2 refers to endoglucanase II, E3 refers to endoglucanase III, C1 refers to exo-cellobiohydrolase I and C2 refers to exo-cellobiohydrolase II.

FIG. 6A is a representation of the *T. longibrachiatum* cbh2 locus, cloned as a 4.1 kb EcoRI fragment on genomic DNA and FIG. 6B is a representation of the cbh2 gene deletion vector pPΔCBHII.

FIG. 7 is an autoradiograph of DNA from *T. longibrachiatum* strain P37PΔCBHIPyr 26 transformed with EcoRI digested pPΔCBHII after Southern blot analysis using a $^{32}P$ labelled pPΔCBHII as the probe. The sizes of molecular weight markers are shown in kilobase pairs to the left of the Figure.

FIG. 8 is a diagram of the plasmid pEGIpyr4.

FIG. 9 is an outline of the construction of plasmid pTEX-EG1.

FIG. 10 illustrates the RBB-CMC activity profile of an acidic EG enriched fungal cellulase composition (CBH I and II deleted) derived from *Trichoderma longibrachiatum* over a pH range at 40° C.; as well as the activity profile of an enriched EG III cellulase composition derived from *Trichoderma longibrachiatum* over a pH range at 40° C.

FIG. 11 illustrates the effect of different cellulase compositions on the redeposition of colorant during the stonewashing process.

DETAILED DESCRIPTION OF THE PREFERRED EMBODIMENTS

As noted above, the methods of this invention are directed toward a method of stonewashing fabrics with fungal cellulase while reducing the amount of backstaining of colorant onto the fabric. The method comprises using a specific fungal cellulase solution substantially free of CBH type components which reduces the backstaining of the colorant onto the fabric. However, prior to discussing this invention in detail, the following terms will first be defined.

1) Definitions:

The term "fabric" refers to sewn or unsewn fabrics, including knits and wovens, made of pure cotton or cotton blends and the like. When cotton blends are employed, the amount of cotton in the fabric should be at least about 40 percent by weight cotton; preferably, more than about 60 percent by weight cotton; and most preferably, more than about 75 percent by weight cotton. When employed as blends, the companion material employed in the fabric can include one or more non-cotton fibers including synthetic fibers such as polyamide fibers (for example, nylon 6 and nylon 66), acrylic fibers (for example, polyacrylonitrile fibers), and polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramid fibers. The fabric typically has been colored with dye or pigment, for instance with the dye indigo. One desirable characteristic of colored fabric is the alteration of colored threads with white threads, for example, in the case of denim this gives denim a white on blue contrast appearance.

The term "stonewashing" means the treatment of dyed denim fabric with a fungal cellulase solution under agitating and cascading conditions, i.e., in a rotary drum washing machine which impart a "stonewashed" appearance to the denim. Methods for imparting a stonewashed appearance to denims are described in U.S. Pat. No. 4,832,864 which is incorporated herein by reference in its entirety.

The term "fungal cellulase" refers to the enzyme composition derived from fungal sources or microorganisms genetically modified so as to incorporate and express all or part of the cellulase genes obtained from a fungal source. Cellulases act on cellulose and its derivatives to hydrolyze cellulose and give primary products, glucose and cellobiose. Fungi capable of producing cellulases useful in preparing cellulase compositions described herein are disclosed in British Patent No. 2 094 826A, the disclosure of which is incorporated herein by reference.

A "redepositing cellulase" as used herein refers to those cellulases which in the enzymatic stonewashing of denim tend to backstain the fabric. Such backstaining of the fabric leads to incomplete stonewashing because instead of the desired blue on white contrast, the redeposition results on blue on blue. Redepositing cellulases include microorganisms such as the fungal microorganism Trichoderma sp. and the like.

Most fungal cellulases generally have their optimum activity in the acidic or neutral pH range although some fungal cellulases are known to possess significant activity under neutral and slightly alkaline conditions, i.e., for example, cellulase derived from *Humicola insolens* is known to have activity in neutral to slightly alkaline conditions.

Fungal cellulases are known to be comprised of several enzyme classifications having different substrate specificity, enzymatic action patterns, and the like. Additionally, enzyme components within each classification can exhibit different molecular weights, different degrees of glycosylation, different isoelectric points, different substrate specificity, etc. For example, fungal cellulases can contain cellulase classifications which include endoglucanases (EGs), exo-cellobiohydrolases (CBHs), β-glucosidases (BGs), etc. On the other hand, while bacterial cellulases are reported in the literature as containing little or no CBH components, there are a few cases where CBH-like components derived from bacterial cellulases have been reported to possess exo-cellobiohydrolase activity.

A fungal cellulase composition produced by a naturally occurring source and which comprises one or more CBH and EG components wherein each of these components is found at the ratio produced by the source is sometimes referred to herein as a "complete fungal cellulase system" or a "complete fungal cellulase composition" to distinguish it from the classifications and components of cellulase isolated therefrom, from incomplete cellulase compositions produced by bacteria and some fungi, or from a cellulase composition obtained from a microorganism genetically modified so as to overproduce, underproduce, or not produce one or more of the CBH type and/or EG type components of cellulase.

The fermentation procedures for culturing fungi for production of cellulase are known per se in the art. For example, cellulase systems can be produced either by solid or submerged culture, including batch, fed-batch and continuous-flow processes. The collection and purification of the cellulase systems from the fermentation broth can also be effected by procedures known per se in the art.

"Endoglucanase ("EG") type components" refer to all of those fungal cellulase components or combination of components which exhibit textile activity properties similar to the endoglucanase components of *Trichoderma longibrachiatum* (previously classified as *Trichoderma reesei*). In this regard, the endoglucanase components of *Trichoderma longibrachiatum* (specifically, EG I, EG II, EG III, and the like either alone or in combination) impart improved feel, improved appearance, softening, color enhancement, and/or a stonewashed appearance to denim fabrics (as compared to the fabric prior to treatment) when these components are incorporated into a textile treatment medium and the fabric is treated with this medium.

Accordingly, endoglucanase type components are those cellulase components which impart improved feel, improved appearance, softening, color enhancement, and/or a stonewashed appearance to denim fabrics (as compared to the fabric before treatment) when these components are incorporated into a medium used to treat the fabrics. Certain EG components may impart reduced strength loss to denim fabrics as compared to the strength loss arising from treatment with a similar cellulase composition but which additionally contains CBH I components.

Such endoglucanase type components may not include components traditionally classified as endoglucanases using activity tests such as the ability of the component (a) to hydrolyze soluble cellulose derivatives such as carboxymethylcellulose (CMC), thereby reducing the viscosity of CMC containing solutions, (b) to readily hydrolyze hydrated forms of cellulose such as phosphoric acid swollen cellulose (e.g., Walseth cellulose) and hydrolyze less readily the more highly crystalline forms of cellulose (e.g., Avicel, Solkafloc, etc.). On the other hand, it is believed that not all endoglucanase components, as defined by such activity tests, will impart one or more of the enhancements to denim fabrics as well as reduced strength loss to denim fabrics. Accordingly, it is more accurate for the purposes herein to define endoglucanase type components as those components of fungal cellulase which possess similar textile activity properties as possessed by the endoglucanase components of *Trichoderma longibrachiatum*.

Fungal cellulases can contain more than one EG type component. The different components generally have different isoelectric points, different molecular weights, different degrees of glycosylation, different substrate specificity, different enzymatic action patterns, etc. The different isoelectric points of the components allow for their separation via ion exchange chromatography and the like. In fact, the isolation of components from different sources is known in the art. See, for example, Bjork et al., U.S. Pat. No. 5,120,463; Schulein et al., International Application WO 89/09259; Wood et al., Biochemistry and Genetics of Cellulose Degradation, pp. 31–52 (1988); Bhat et al., Carbohydrate Research, Vol. 190, pp. 279–297 (1989); Schulein, Methods in Enzymology, Vol. 160, pp. 234–242 (1988); and the like. The entire disclosure of each of these references is incorporated herein by reference.

Preferably the fungal cellulase compositions of the present invention include substantially pure EG I or EG III cellulase components. It is contemplated that the fungal cellulase composition of the present invention may include substantially pure EG II cellulase component. However, it is also contemplated that combinations of EG type components may give a synergistic response in reducing the amount of backstaining of dye onto denim during the stonewashing of denim. On the other hand, a single EG type component may be more stable or have a broader spectrum of activity over a range of pHs. Further these anti-redeposition properties may be enhanced for one or more specific EG type components. Accordingly, the EG type components employed in this invention can be either a single EG type component or a combination of two or more EG type components. When a combination of components is employed, the EG type component may be derived from the same or different sources.

It is possible that proteins other than CBH type cellulase components present in the whole cellulase composition may cause redeposition of colorant onto the fabric during the stonewashing process. Therefore, it is comtemplated that the use of substantially pure EG I, EG II or EG III components may eliminate some or all of these proteins present in the whole cellulase composition and may result in a further reduction in redeposition.

The term "substantially pure EG cellulase" refers to a composition of cellulase proteins containing at least 40 weight percent, preferably at least 70 weight percent and most preferably at least 90 weight percent of the particular EG type component specified based on the total weight of the cellulase proteins.

The term "EG I cellulase" refers to the endoglucanase component derived from Trichoderma spp. characterized by a pH optimum of about 4.0 to 6.0, and isoelectric point (pI) of from about 4.5 to 5.3, and a molecular weight of about 47 to 50 Kdaltons. Preferably, EG I cellulase is derived from either *Trichoderma longibrachiatum* or from *Trichoderma viride*. EG I cellulase derived from *Trichoderma longibrachiatum* has a pH optimum of about 5.0, an isoelectric point (pI) of about 4.7 and a molecular weight of about 47 to 49 Kdaltons. EG I cellulase derived from *Trichoderma viride* has a pH optimum of about 5.0, an isoelectric point (pI) of about 5.3 and a molecular weight of about 50 Kdaltons.

It is noted that EG II has been previously referred to by the nomenclature "EG III" by some authors but current nomenclature uses the term EG II. In any event the EG II protein is substantially different from the EG III protein in its molecular weight, pI and pH optimum. The term "EG II cellulase" refers to the endoglucanase component derived from Trichoderma spp. characterized by a pH optimum of about 4.0 to 6.0, and isoelectric point (pI) of from about 5.5, and a molecular weight of about 35 Kdaltons. Preferably, EG II cellulase is derived from either *Trichoderma longibrachiatum* or from *Trichoderma viride*.

The term "EG III cellulase" refers to the endoglucanase component derived from Trichoderma spp. characterized by a pH optimum of about 5.0 to 7.0, and isoelectric point (pI) of from about 7.2 to 8.0, and a molecular weight of about 23 to 28 Kdaltons. Preferably, EG III cellulase is derived from either *Trichoderma longibrachiatum* or from *Trichoderma viride*. EG III cellulase derived from *Trichoderma longibrachiatum* has a pH optimum of about 5.5 to 6.0, an isoelectric point (pI) of about 7.4 and a molecular weight of about 25 to 28 Kdaltons. EG III cellulase derived from *Trichoderma viride* has a pH optimum of about 5.5, an isoelectric point (pI) of about 7.7 and a molecular weight of about 23.5 Kdaltons.

It is contemplated that EG type components can be derived from bacterially derived cellulases.

"Exo-cellobiohydrolase type ("CBH type") components" refer to those fungal cellulase components which exhibit textile activity properties similar to CBH I and/or CBH II cellulase components of *Trichoderma longibrachiatum*. In this regard, when used in the absence of EG type cellulase components (as defined above), the CBH I and CBH II components of *Trichoderma longibrachiatum* alone do not impart any significant enhancements in feel, appearance, color enhancement and/or stonewashed appearance to the so treated denim fabrics. Additionally, when used in combination with some EG type components, in a ratio of approximately 2.5:1 of CBH I to EG components, the CBH I component of *Trichoderma longibrachiatum* imparts enhanced strength loss to the denim fabrics.

Accordingly, CBH I type components and CBH II type components refer to those fungal cellulase components which exhibit textile activity properties similar to CBH I and CBH II components of *Trichoderma longibrachiatum*, respectively. As noted above, for CBH I type components, this includes the property of enhancing strength loss of denim fabrics when used in the presence of certain EG type components.

Such exo-cellobiohydrolase type components may not include components traditionally classed as exo-cellobiohydrolases using activity tests such as those used to characterize CBH I and CBH II from *Trichoderma longibrachiatum*. For example, such components (a) are competitively inhibited by cellobiose ($K_i$ approximately 1 mM); (b) are unable to hydrolyze to any significant degree substituted celluloses, such as carboxymethylcellulose, etc., and (c) hydrolyze phosphoric acid swollen cellulose and to a lesser degree highly crystalline cellulose. On the other hand, it is believed that some cellulase components which are characterized as CBH components by such activity tests, will impart improved feel, appearance, softening, color enhancement, and/or a stonewashed appearance to cotton-containing fabrics when used alone in the cellulase composition. Accordingly, it is believed to be more accurate for the purposes herein to define such exo-cellobiohydrolases as EG type components because these components possess similar functional properties in textile uses as possessed by the endoglucanase components of *Trichoderma longibrachiatum*.

As used herein, the term "fungal cellulase composition substantially free of CBH type cellulase components" means that the cellulase composition, based on the weight of protein, will contain less than 20 weight percent CBH type components, more preferably less than 10 weight percent of CBH type cellulase components. It has been unexpectedly found that the presence of CBH type components is not required to achieve a stonewashed appearance. However, it is contemplated that a small amount (i.e., less than 20%) may provide some enhancement of stonewashing. It has also been found that the removal of CBH type components from the cellulase reduces the redeposition of colorant. Without being limited to any theory, the CBH type components may reversibly sequester the colorant because they are proteins and because of their affinity for cellulase and it is contemplated that other proteins may have a similar effect.

Cellulase compositions substantially free of CBH type components can be obtained by purification techniques. Specifically, the complete cellulase system can be purified into substantially pure components by recognized separation techniques well published in the literature, including ion exchange chromatography at a suitable pH, affinity chromatography, size exclusion and the like. For example, in ion exchange chromatography (usually anion exchange chromatography), it is possible to separate the cellulase components by eluting with a pH gradient, or a salt gradient, or both a pH and a salt gradient. After purification, the requisite amount of the desired components could be recombined.

It is also contemplated that mixtures of cellulase compositions substantially free of CBH type components could be prepared by means other than isolation and recombination of the components. In this regard, recombinant techniques can alter the relative ratio of EG type components to CBH type components produced by the organism so as to produce a cellulase composition substantially free of CBH type components.

In regard to the above, a preferred method for the preparation of cellulase compositions described herein is by genetically modifying a microorganism so as to overproduce one or more EG type components. Likewise, it is also possible to genetically modify a microorganism so as to be incapable of producing one or more CBH type components which methods do not produce any heterologous protein.

In regard to the above, U.S. Ser. No. 07/770,049, filed Oct. 4, 1991 which is a continuation-in-part of U.S. Ser. No. 07/593,919, filed Oct. 5, 1990 and both of which are incorporated herein by reference in their entirety, disclose methods for genetically engineering *Trichoderma longibrachiatum* so as to be incapable of producing one or more CBH components and/or overproducing one or more EG components. Moreover, the methods of that application create *Trichoderma longibrachiatum* strains which do not produce any heterologous proteins. Likewise, Miller et al., "Direct and Indirect Gene Replacement in *Aspergillus nidulans*", *Molecular and Cellular Biology*, p. 1714–1721 (1985) discloses methods for deleting genes in *Aspergillus nidulans* by DNA mediated transformation using a linear fragment of homologous DNA.

In view of the above, the deletion of the genes responsible for producing CBH I type and/or CBH II type cellulase components would have the effect of enriching the amount of EG components present in the cellulase composition.

"β-Glucosidase (BG) components" refer to those components of cellulase which exhibit BG activity; that is to say that such components will act from the non-reducing end of cellobiose and other soluble cellooligosaccharides ("cellobiose") and give glucose as the sole product. BG components do not adsorb onto or react with cellulose polymers. Furthermore, such BG components are competitively inhibited by glucose ($K_i$ approximately 1 mM). While in a strict sense, BG components are not literally cellulases because they cannot degrade cellulose, such BG components are included within the definition of the cellulase system because these enzymes facilitate the overall degradation of cellulose by further degrading the inhibitory cellulose degradation products (particularly cellobiose) produced by the combined action of CBH type components and EG type components.

Methods to either increase or decrease the amount of BG components in the cellulase composition are disclosed in U.S. Ser. No. 07/807,028, filed Dec. 10, 1991 which is a continuation-in-part of U.S. Ser. No. 07/625,140, filed Dec. 10, 1990, as Attorney Docket No. 010055-056 and entitled "SACCHARIFICATION OF CELLULOSE BY CLONING AND AMPLIFICATION OF THE β-GLUCOSIDASE GENE OF TRICHODERMA REESEI," both of which applications are incorporated herein by reference in their entirety.

Preferred fungal cellulases for use in preparing the cellulase compositions used in this invention are those obtained from *Trichoderma longibrachiatum*, *Trichoderma viride*, *Trichoderma koningii*, Pencillium sp., *Humicola insolent*, Aspergillus sp. and the like. Certain fungal cellulases are commercially available, i.e., CELLUCAST (available from Novo Industry, Copenhagen, Denmark), RAPIDASE (available from Gist Brocades, N.V., Delft, Holland), CYTOLASE 123 (available from Genencor International, South San Francisco, Calif.) and the like. Other fungal cellulases can be readily isolated by art recognized fermentation and isolation procedures.

The term "buffer" refers to art recognized acid/base reagents which stabilize the cellulase solution against undesired pH shifts during the cellulase treatment of the denim fabric. In this regard, it is art recognized that cellulase activity is pH dependent. That is to say that a specific cellulase composition will exhibit cellulolytic activity within a defined pH range with optimal cellulolytic activity generally being found within a small portion of this defined range. The specific pH range for cellulolytic activity will vary with each cellulase composition. As noted above, while most cellulases will exhibit cellulolytic activity within an acidic to neutral pH profile, there are some cellulase compositions which exhibit cellulolytic activity in an alkaline pH profile.

During cellulase stonewashing treatment of the denim fabric, it is possible that the pH of the initial cellulase solution could be outside the range required for cellulase activity. It is further possible for the pH to change during treatment of the denim fabric, for example, by the generation of a reaction product which alters the pH of the solution. In either event, the pH of an unbuffered cellulase solution could be outside the range required for cellulolytic activity. When this occurs, undesired reduction or cessation of cellulolytic activity in the cellulase solution occurs. For example, if a cellulase having an acidic activity profile is employed in a neutral unbuffered aqueous solution, then the pH of the solution will result in lower cellulolytic activity and possibly in the cessation of cellulolytic activity. On the other hand, the use of a cellulase having a neutral or alkaline pH profile in a neutral unbuffered aqueous solution should initially provide significant cellulolytic activity.

In view of the above, the pH of the cellulase solution should be maintained within the range required for cellulolytic activity. One means of accomplishing this is by simply monitoring the pH of the system and adjusting the pH as required by the addition of either an acid or a base. However, in a preferred embodiment, the pH of the system is preferably maintained within the desired pH range by the use of a buffer in the cellulase solution. In general, a sufficient amount of buffer is employed so as to maintain the pH of the solution within the range wherein the employed cellulase exhibits activity. Insofar as different cellulase compositions have different pH ranges for exhibiting cellulase activity, the specific buffer employed is selected in relationship to the specific cellulase composition employed. The buffer(s) selected for use with the cellulase composition employed can be readily determined by the skilled artisan taking into account the pH range and optimum for the cellulase composition employed as well as the pH of the cellulase solution. Preferably, the buffer employed is one which is compatible with the cellulase composition and which will maintain the pH of the cellulase solution within the pH range required for optimal activity. Suitable buffers include sodium citrate, ammonium acetate, sodium acetate, disodium phosphate, and any other art recognized buffers.

2. Methodology

As noted above, the present invention is an improvement over prior art methods for stonewashing denim fabrics insofar as the present invention employs a specific cellulase composition which minimizes redeposition of colorant.

It is contemplated that the methods of this invention will provide additional enhancements to the fabric such as improvements in the feel and/or appearance of the fabric, while reducing strength loss in the treated fabric.

The cellulase compositions described above are preferably employed in a final aqueous treatment solution which contains cellulase and other optional ingredients including, for example, a buffer, a surfactant, a scouring agent, and the like.

The concentration of the cellulase composition employed in this final solution is generally a concentration sufficient for its intended purpose. That is to say that an amount of the cellulase composition is employed to provide effective stonewashing of the denim fabric. Thus an "effective amount" of cellulase composition is that amount which will provide stonewashing. The amount of the cellulase composition employed is also dependent on the equipment employed, the process parameters employed (the temperature of the cellulase treatment solution, the exposure time to the cellulase solution, and the like), the cellulase activity (e.g., a cellulase solution will require a lower concentration of a more active cellulase composition as compared to a less active cellulase composition), and the like. The exact concentration of the cellulase composition can be readily determined by the skilled artisan based on the above factors as well as the desired effect. Preferably, the concentration of the cellulase composition in the final cellulase solution employed herein is from about 5 mgs/liter of cellulase solution to about 2000 mgs/liter of cellulase solution; and more preferably, from about 10 mgs/liter of cellulase solution to about 200 mgs/liter of cellulase solution. (The cellulase concentration recited above refers to the weight of total protein).

When a buffer is employed in the cellulase treatment solution, the concentration of buffer in the aqueous cellulase treatment solution is that which is sufficient to maintain the pH of the solution within the range wherein the employed cellulase exhibits activity which, in turn, depends on the nature of the cellulase employed. The exact concentration of buffer employed will depend on several factors which the skilled artisan can readily take into account. For example, in a preferred embodiment, the buffer as well as the buffer concentration are selected so as to maintain the pH of the final cellulase solution within the pH range required for optimal cellulase activity. In general, buffer concentration in the cellulase solution is about 0.005N and greater. Preferably, the concentration of the buffer in the cellulase solution is from about 0.01 to about 0.2N.

In addition to cellulase and a buffer, the cellulase treatment solution can optionally contain a surfactant, i.e., less than about 10,000 ppm, and preferably from about 10 ppm to about 1,000 ppm. Suitable surfactants include any surfactant compatible with the cellulase and the fabric including, for example, anionic, non-ionic and ampholytic surfactants.

Suitable anionic surfactants for use herein include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3.

Ampholytic surfactants include quaternary ammonium salt sulfonates, betaine-type ampholytic surfactants, and the like. Such ampholytic surfactants have both the positive and negative charged groups in the same molecule.

Nonionic surfactants generally comprise polyoxyalkylene ethers, as well as higher fatty acid alkanolamides or alkylene oxide adduct thereof, fatty acid glycerine monoesters, and the like.

Mixtures of surfactants can also be employed.

In a preferred embodiment, a concentrate can be prepared for use in the methods described herein. Such concentrates would contain concentrated amounts of the cellulase composition described above, buffer and surfactant, preferably in an aqueous solution. When so formulated, the concentrate can readily be diluted with water so as to quickly and accurately prepare cellulase solutions having the requisite concentration of these additives. Preferably, such concentrates will comprise from about 0.5 to about 50 weight percent of a fungal cellulase composition described above (protein); from about 1 to about 80 weight percent buffer; from about 0 to about 50 weight percent surfactant; with the balance being water. When aqueous concentrates are formulated, these concentrates can be diluted so as to arrive at the requisite concentration of the components in the cellulase solution as indicated above. As is readily apparent, such concentrates will permit facile formulation of the cellulase solutions as well as permit feasible transportation of the concentration to the location where it will be used. The concentrate can be either in the form of liquid, emulsion, gel, paste, and the like. Such forms are well known to the skilled artisan.

When a solid cellulase concentrate is employed, the cellulase composition is generally a granule, a powder, an agglomerate and the like. When granules are used, the granules are preferably formulated so as to contain a cellulase protecting agent. See, for instance, U.S. Ser. No. 07/642,669, filed Jan. 17, 1991 as Attorney Docket No. 010055-073 and entitled "GRANULES CONTAINING BOTH AN ENZYME AND AN ENZYME PROTECTING AGENT AND DETERGENT COMPOSITIONS CONTAINING SUCH GRANULES," which application is incorporated herein by reference in its entirety. Likewise, the granules can be formulated so as to contain materials to reduce the rate of dissolution of the granules into the wash medium. Such materials and granules are disclosed in U.S. Ser. No. 07/642,596 filed on Jan. 17, 1991 as Attorney Docket No. GCS-171-US1 and entitled "GRANULAR COMPOSITIONS," which application is incorporated herein by reference in its entirety.

Other materials can also be used with or placed in the cellulase composition as desired, including stones, fillers, solvents, enzyme activators, other anti-redeposition agents and the like.

The liquor ratios, i.e., the ratio of weight of cellulase treatment solution to the weight of fabric, employed herein is generally an amount sufficient to achieve the desired stonewashing effect in the denim fabric and is dependent upon the process used. Preferably, the liquor ratios are generally from about 1:1 and greater, and more preferably greater than about 2:1. Use of liquor ratios of greater than about 20:1 are usually not preferred from an economic viewpoint.

Reaction temperatures for cellulase treatment are governed by two competing factors. Firstly, higher temperatures generally correspond to enhanced reaction kinetics, i.e., faster reactions, which permit reduced reaction times as compared to reaction times required at lower temperatures. Accordingly, reaction temperatures are generally at least about 30° C. and greater. Secondly, cellulase is a protein which loses activity beyond a given reaction temperature which temperature is dependent on the nature of the cellulase used. Thus, if the reaction temperature is permitted to go too high, then the cellulolytic activity is lost as a result of the denaturing of the cellulase. As a result, the maximum reaction temperatures employed herein are generally about 65° C. In view of the above, reaction temperatures are generally from about 30° C. to about 65° C.; preferably, from about 35° C. to about 60° C.; and more preferably, from about 35° C. to about 55° C.

Reaction times are generally from about 10 minutes to about 3 hours and, preferably, from about 20 minutes to about 1 hour.

The denim fabrics stonewashed in the methods described above using such cellulase compositions show reduced deposition of dye as compared to the same denim fabric stonewashed in the same manner with a complete cellulase composition.

The following examples are offered to illustrate the present invention and should not be construed in any way as limiting its scope.

EXAMPLES

Examples 1–14 demonstrate the preparation of *Trichoderma longibrachiatum* genetically engineered so as to be incapable of producing one or more cellulase components or so as to overproduce specific cellulase components.

EXAMPLE 1

Selection for pyr4⁻ derivatives of *Trichoderma longibrachiatum*

The pyr4 gene encodes orotidine-5'-monophosphate decarboxylase, an enzyme required for the biosynthesis of uridine. The toxic inhibitor 5-fluoroorotic acid (FOA) is incorporated into uridine by wild-type cells and thus poisons the cells. However, cells defective in the pyr4 gene are resistant to this inhibitor but require uridine for growth. It is, therefore, possible to select for pyr4 derivative strains using FOA. In practice, spores of *T. longibrachiatum* (previously classified as *T. reesei*) strain RL-P37 (Sheir-Neiss, G. and Montenecourt, B. S., *Appl. Microbiol. Biotechnol.* 20, p. 46–53 (1984)) were spread on the surface of a solidified medium containing 2 mg/ml uridine and 1.2 mg/ml FOA. Spontaneous FOA-resistant colonies appeared within three to four days and it was possible to subsequently identify those FOA-resistant derivatives which required uridine for growth. In order to identify those derivatives which specifically had a defective pyr4 gene, protoplasts were generated and transformed with a plasmid containing a wild-type pyr4 gene (see Examples 3 and 4). Following transformation, protoplasts were plated on medium lacking uridine. Subsequent growth of transformed colonies demonstrated complementation of a defective pyr4 gene by the plasmid-borne pyr4 gene. In this way, strain GC69 was identified as a pyr4⁻ derivative of strain RL-P37.

EXAMPLE 2

Preparation of CBHI Deletion Vector

A cbh1 gene encoding the CBHI protein was cloned from the genomic DNA of *T. longibrachiatum* strain RL-P37 by hybridization with an oligonucleotide probe designed on the basis of the published sequence for this gene using known probe synthesis methods (Shoemaker et al., 1983b). The cbh1 gene resides on a 6.5 kb PstI fragment and was inserted into PstI cut pUC4K (purchased from Pharmacia Inc., Piscataway, N.J.) replacing the Kan$^r$ gene of this vector using techniques known in the art, which techniques are set forth in Sambrook et al. (1989) MOLECULAR CLONING A LABORATORY MANUAL, Cold Spring Harbor Press, and incorporated herein by reference. The resulting plasmid, pUC4K::cbh1 was then cut with HindIII and the larger fragment of about 6 kb was isolated and religated to give pUC4K::cbh1ΔH/H (see FIG. 1). This procedure removes the entire cbh1 coding sequence and approximately 1.2 kb upstream and 1.5 kb downstream of flanking sequences. Approximately, 1 kb of flanking DNA from either end of the original pstI fragment remains.

The *T. longibrachiatum* pyr4 gene was cloned as a 6.5 kb HindIII fragment of genomic DNA in pUC18 to form pTpyr2 (Smith et al., 1991 *Curr Genet.*, 19:27–33) following the methods of Sambrook et al., supra. The plasmid pUC4K::cbh1ΔH/H was cut with HindIII and the ends were dephosphorylated with calf intestinal alkaline phosphatase. This end dephosphorylated DNA was ligated with the 6.5 kb HindIII fragment containing the *T. longibrachiatum* pyr4 gene to give pΔCBHIpyr4. FIG. 1 illustrates the construction of this plasmid.

Digestion of pΔCBHIpyr4 with EcoRI liberated a larger fragment which consisted of flanking regions of the cbh1 locus at either end with the pyr4 gene replacing the cbh1 coding sequence in the center. The only DNA on this fragment which was not derived from *T. longibrachiatum* was a 21 bp fragment derived from the multiple cloning site of pUC4K.

EXAMPLE 3

Isolation of Protoplasts

Mycelium was obtained by inoculating 100 ml of YEG (0.5% yeast extract, 2% glucose) in a 500 ml flask with about 5×10$^7$ T. longibrachiatum GC69 spores (the pyr4 derivative strain). The flask was then incubated at 37° C. with shaking for about 16 hours. The mycelium was harvested by centrifugation at 2,750×g. The harvested mycelium was further washed in a 1.2 M sorbitol solution and resuspended in 40 ml of a solution containing 5 mg/ml Novozym® 234 solution (which is the trade name for a multicomponent enzyme system containing 1,3-alpha-glucanase, 1,3-beta-glucanase, laminarinase, xylanase, chitinase and protease from Novo Biolabs, Danbury, Conn.); 5 mg/ml MgSO$_4$.7H$_2$O; 0.5 mg/ml bovine serum albumin; 1.2 M sorbitol. The protoplasts were removed from the cellular debris by filtration through Miracloth (Calbiochem Corp, La Jolla, Calif.) and collected by centrifugation at 2,000×g. The protoplasts were washed three times in 1.2 M sorbitol and once in 1.2 M sorbitol, 50 mM CaCl$_2$, centrifuged and resuspended at a density of approximately 2×10$^8$ protoplasts per ml of 1.2 M sorbitol, 50 mM CaCl$_2$.

EXAMPLE 4

Transformation of Fungal Protoplasts with pΔCBHIpyr4

200 µl of the protoplast suspension prepared in Example 3 was added to 20 µl of EcoRI digested pΔCBHIpyr4 (prepared in Example 2) in TE buffer (10 mM Tris, pH 7.4; 1 mM EDTA) and 50 µl of a polyethylene glycol (PEG) solution containing 25% PEG 4000, 0.6 M KCl and 50 mM CaCl$_2$. This mixture was incubated on ice for 20 minutes. After this incubation period 2.0 ml of the above-identified PEG solution was added thereto, the solution was further mixed and incubated at room temperature for 5 minutes. After this second incubation, 4.0 ml of a solution containing 1o2 M sorbitol and 50 mM CaCl$_2$ was added thereto and this solution was further mixed. The protoplast solution was then immediately added to molten aliquots of Vogel's Medium N (3 grams sodium citrate, 5 grams KH$_2$PO$_4$, 2 grams NH$_4$NO$_3$, 0.2 grams MgSO$_4$.7H$_2$O, 0.1 gram CaCl$_2$.2H$_2$O, 5 µg α-biotin, 5 mg citric acid, 5 mg ZnSO$_4$.7H$_2$O, 1 mg Fe(NH$_4$)$_2$.6H$_2$O, 0.25 mg CuSO$_4$.5H$_2$O, 50 µg MnSO$_4$.4H$_2$O per liter) containing an additional 1% glucose, 1.2 M sorbitol and 1% agarose. The protoplast/ medium mixture was then poured onto a solid medium containing the same Vogel's medium as stated above. No uridine was present in the medium and therefore only transformed colonies were able to grow as a result of complementation of the pyr4 mutation of strain GC69 by the wild type pyr4 gene insert in pΔCBHIpyr4. These colonies were subsequently transferred and purified on a solid Vogel's medium N containing as an additive, 1% glucose and stable transformants were chosen for further analysis.

At this stage stable transformants were distinguished from unstable transformants by their faster growth rate and formation of circular colonies with a smooth, rather than ragged outline on solid culture medium lacking uridine. In some cases a further test of stability was made by growing the transformants on solid non-selective medium (i.e. containing uridine), harvesting spores from this medium and determining the percentage of these spores which will subsequently germinate and grow on selective medium lacking uridine.

EXAMPLE 5

Analysis of the Transformants

DNA was isolated from the transformants obtained in Example 4 after they were grown in liquid Vogel's medium N containing 1% glucose. These transformant DNA samples were further cut with a PstI restriction enzyme and subjected to agarose gel electrophoresis. The gel was then blotted onto a Nytran membrane filter and hybridized with a $^{32}$P labelled pΔCBHIpyr4 probe. The probe was selected to identify the native cbh1 gene as a 6.5 kb PstI fragment, the native pyr4 gene and any DNA sequences derived from the transforming DNA fragment.

The radioactive bands from the hybridization were visualized by autoradiography. The autoradiograph is seen in FIG. 3. Five samples were run as described above, hence samples A, B, C, D, and E. Lane E is the untransformed strain GC69 and was used as a control in the present analysis. Lanes A–D represent transformants obtained by the methods described above. The numbers on the side of the autoradiograph represent the sizes of molecular weight markers. As can be seen from this autoradiograph, lane D does not contain the 6.5 kb CBHI band, indicating that this gene has been totally deleted in the transformant by integration of the DNA fragment at the cbh1 gene. The cbh1 deleted strain is called P37PΔCBHI. FIG. 2 outlines the deletion of the T. longibrachiatum cbh1 gene by integration through a double cross-over event of the larger EcoRI fragment from pΔCBHIpyr4 at the cbh1 locus on one of the T. longibrachiatum chromosomes. The other transformants analyzed appear identical to the untransformed control strain.

EXAMPLE 6

Analysis of the Transformants with pIntCBHI

The same procedure was used in this example as in Example 5, except that the probe used was changed to a $^{32}$P labelled pIntCBHI probe. This probe is a pUC-type plasmid containing a 2 kb BglII fragment from the cbh1 locus within the region that was deleted in pUC4K::cbh1ΔH/H. Two samples were run in this example including a control, sample A, which is the untransformed strain GC69 and the transformant P37PΔCBHI, sample B. As can be seen in FIG. 4, sample A contained the cbh1 gene, as indicated by the band at 6.5 kb; however the transformant, sample B, does not contain this 6.5 kb band and therefore does not contain the cbh1 gene and does not contain any sequences derived from the pUC plasmid.

EXAMPLE 7

Protein Secretion by Strain P37PΔCBHI

Spores from the produced P37PΔCBHI strain were inoculated into 50 ml of a Trichoderma basal medium containing 1% glucose, 0.14% $(NH_4)_2SO_4$, 0.2% $KH_2PO_4$, 0.03% $MgSO_4$, 0.03% urea, 0.75% bactotryptone, 0.05% Tween 80, 0.000016% $CuSO_4 \cdot 5H_2O$, 0.001% $FeSO_4 \cdot 7H_2O$, 0.000128% $ZnSO_4 \cdot 7H_2O$, 0.0000054% $Na_2MoO_4 \cdot 2H_2O$, 0.0000007% $MnCl \cdot 1.4H_2O$. The medium was incubated with shaking in a 250 ml flask at 37° C. for about 48 hours. The resulting mycelium was collected by filtering through Miracloth (Calbiochem Corp.) and washed two or three times with 17 mM potassium phosphate. The mycelium was finally suspended in 17 mM potassium phosphate with 1 mM sophorose and further incubated for 24 hours at 30° C. with shaking. The supernatant was then collected from these cultures and the mycelium was discarded. Samples of the culture supernatant were analyzed by isoelectric focusing using a Pharmacia Phastgel system and pH 3–9 precast gels according to the manufacturer's instructions. The gel was stained with silver stain to visualize the protein bands. The band corresponding to the cbh1 protein was absent from the sample derived from the strain P37PΔCBHI, as shown in FIG. 5. This isoelectric focusing gel shows various proteins in different supernatant cultures of T. longibrachiatum. Lane A is partially purified CBHI; Lane B is the supernatant from an untransformed T. longibrachiatum culture; Lane C is the supernatant from strain P37PΔCBHI produced according to the methods of the present invention. The position of various cellulase components are labelled CBHI, CBHII, EGI, EGII, and EGIII. Since CBHI constitutes 50% of the total extracellular protein, it is the major secreted protein and hence is the darkest band on the gel. This isoelectric focusing gel clearly shows depletion of the CBHI protein in the P37PΔCBHI strain.

EXAMPLE 8

Preparation of pPΔCBHII

The cbh2 gene of T. longibrachiatum, encoding the CBHII protein, has been cloned as a 4.1 kb EcoRI fragment of genomic DNA which is shown diagrammatically in FIG. 6A (Chen et al., 1987, Biotechnology, 5:274–278). This 4.1 kb fragment was inserted between the EcoRI sites of pUC4XL. The latter plasmid is a pUC derivative (constructed by R. M. Berka, Genencor International, Inc.) which contains a multiple cloning site with a symmetrical pattern of restriction endonuclease sites arranged in the order shown here: EcoRI, BamHI, SacI, SmaI, HindIII, XhoI, BglII, ClaI, BglII, XhoI, HindIII, SmaI, SacI, BamHI, EcoRI. Using methods known in the art, a plasmid, pPΔCBHII (FIG. 6B), has been constructed in which a 1.7 kb central region of this gene between a HindIII site (at 74 bp 3' of the CBHII translation initiation site) and a ClaI site (at 265 bp 3' of the last codon of CBHII) has been removed and replaced by a 1.6 kb HindIII- ClaI DNA fragment containing the T. longibrachiatum pyr4 gene.

The T. longibrachiatum pyr4 gene was excised from pTpyr2 (see Example 2) on a 1.6 kb NheI-SphI fragment and inserted between the SphI and XbaI sites of pUC219 to create p219M (Smith et al., 1991, Curr. Genet 19 p. 27–33). The vector pUC219 is derived from pUC119 (described by Wilson et al. (1984) Gene 77:69–78) by expanding the multiple cloning site to include restriction sites for BglII, ClaII and XhoI. The pyr4 gene was removed from p219M as a HindIII-ClaI fragment having seven bp of DNA at one end and six bp of DNA at the other end derived from the pUC219 multiple cloning site and inserted into the HindIII and ClaI sites of the cbh2 gene to form the plasmid pPΔCBHII (see FIG. 6B).

Digestion of this plasmid with EcoRI will liberate a fragment having 0.7 kb of flanking DNA from the cbh2 locus at one end, 1.7 kb of flanking DNA from the cbh2 locus at the other end and the T. longibrachiatum pyr4 gene in the middle.

EXAMPLE 9

Generation of a pyr4⁻ Derivative of P37PΔCBHI

Spores of the transformant (P37PΔCBHI) which was deleted for the cbh1 gene were spread onto medium containing FOA. A pyr4⁻derivative of this transformant was subsequently obtained using the methods of Example 1. This pyr4⁻strain was designated P37PΔCBHIPyr⁻26. Southern analysis has shown that a spontaneous deletion had occurred when strain P37PΔCBHIPyr⁻26 was selected. This deletion completely removed the pyr4 gene which had integrated at the cbh1 locus beyond the extent of the 6.5 kb PstI fragment of genomic DNA which was originally cloned.

EXAMPLE 10

Deletion of the cbh2 gene in a strain previously deleted for cbh1

Protoplasts of strain P37PΔCBHIPyr⁻26 were generated and transformed with EcoRI digested pPΔCBHII according to the methods outlined in Examples 3 and 4.

Purified stable transformants were cultured in shaker flasks as in Example 7 and the protein in the culture supernatants was examined by isoelectric focusing. One transformant (designated P37PΔΔCBH67) was identified which did not produce any CBHII (nor CBH I) protein. Lane D of FIG. 5 shows the supernatant from a transformant deleted for both the cbh1 and cbh2 genes produced according to the methods of the present invention.

DNA was extracted from strain P37PΔΔCBH67, digested with EcoRI and Asp718, and subjected to agarose gel electrophoresis. The DNA from this gel was blotted to a membrane filter and hybridized with $^{32}$P labelled pPΔCBHII (FIG. 7). Lane A of FIG. 7 shows the hybridization pattern observed for DNA from an untransformed T. longibrachiatum strain. The 4.1 kb EcoRI fragment containing the wild-type cbh2 gene was observed. Lane B shows the hybridization pattern observed for strain P37PΔΔCBH67. The single 4.1 kb band has been eliminated and replaced by two bands of approximately 0.9 and 3.1 kb. This is the expected pattern if a single copy of the EcoRI fragment from pPΔCBHII had integrated precisely at the cbh2 locus.

The same DNA samples were also digested with EcoRI and Southern blot analysis was performed as above. In this Example, the probe was $^{32}$P labelled pIntCBHII. This plasmid contains a portion of the cbh2 gene coding sequence from within that segment of the cbh2 gene which was deleted in plasmid pPΔCBHII. No hybridization was seen with DNA from strain P37PΔΔCBH67 showing that the cbh2 gene was deleted and that no sequences derived from the pUC plasmid were present in this strain.

EXAMPLE 11

Selection of a pyr4 null mutant of strain P37PΔΔCBH67

Spores of the transformant (P37PΔΔCBH67) which was deleted for both the cbh1 and cbh2 genes were spread onto medium containing FOA. A pyr4 deficient derivative of this transformant was subsequently obtained using the methods described in Example 1. This pyr4 deficient strain was designated P37PΔΔCBH67Pyr⁻1. Southern analysis has shown that a spontaneous deletion had occurred when strain P37PΔΔCBH67Pyr⁻1was selected. This deletion completely removed the pyr4 gene which had integrated at the cbh2 locus beyond the extent of the 4.1 kb EcoRI fragment of genomic DNA which was originally cloned. The short (6 bp and 7 bp) fragments of DNA derived from the pUC219 multiple cloning site which were present at either end of the pyr4 gene would also have been removed from the genome by this deletion.

EXAMPLE 12

Construction of pEGIpyr4

The T. longibrachiatum egl1 gene, which encodes EGI, has been cloned as a 4.2 kb HindIII fragment of genomic DNA from strain RL-P37 by hybridization with oligonucleotides synthesized according to the published sequence (Penttila et al., 1986, Gene 45:253–263; van Arsdell et al., 1987, Bio/Technology 5:60–64). A 3.6 kb HindIII-BamHI fragment was taken from this clone and ligated with a 1.6 kb HindIII-BamHI fragment containing the T. longibrachiatum pyr4 gene obtained from pTpyr2 (see Example 2) and pUC218 (identical to pUC219, see Example 8, but with the multiple cloning site in the opposite orientation) cut with HindIII to give the plasmid pEGIpyr4 by standard molecular techniques as outlined in Sambrook et al. (1989), supra (FIG. 8). Digestion of pEGIpyr4 with HindIII would liberate a fragment of DNA containing only T. longibrachiatum genomic DNA (the egl1 and pyr4 genes) except for 24 bp of sequenced, synthetic DNA between the two genes and 6 bp of sequenced, synthetic DNA at one end (see FIG. 8). Both these pieces of synthetic DNA were obtained from the multiple cloning site of pUC-type vectors.

EXAMPLE 13

Construction of the EGI expression vector pTEX-EG1

The plasmid, pTEX-EGI was constructed following the methods of Sambrook et al. (1989), supra, and is illustrated in FIG. 9. This plasmid has been designed as a multi-purpose expression vector for use in the filamentous fungus Trichoderma longibrachiatum. The expression cassette has several unique features that make it useful for this function. Transcription is regulated using the strong CBHI gene promoter and terminator sequences for T. longibrachiatum. Between the CBHI promoter and terminator there are unique PmeI and Sst I restriction sites that are used to insert the gene to be expressed. The T. longibrachiatum pyr4 selectable marker gene has been inserted into the CBHI terminator and the whole expression cassette (CBHI promoter-insertion sites-CBHI terminator-pyr4 gene-CBHI terminator) can be excised utilizing the unique NotI restriction site or the unique NotI and NheI restriction sites.

This vector is based on the bacterial vector, pSL1180 (Pharmacia Inc., Piscataway, N.J.), which is a pUC-type vector with an extended multiple cloning site. pTEX was digested with SstII and PmeI and then ligated with a synthetic DNA linker designed to join the cbh1 promoter with the egl1 coding sequence and with an approximately 2 kb SfiI-ScaI fragment of T. longibrachiatum DNA containing most of the egl1 coding sequence and the terminator region. This ligation produced the vector pTEX-EGI. This vector was digested with NotI and NheI to release the expression cassette which comprised the following components:

a) 11 bp of linker DNA derived from the multiple cloning site of pSL1180.

b) An approximately 2.2 kb PstI-SstII fragment of T. longibrachiatum DNA from the promoter region of the cbh1 gene. The SstII site is at a position 15 bp 5' of the translation initiation codon (ATG).

c) A synthetic DNA linker used to join the cbh1 promoter with the egl1 coding sequence, having single-stranded overhanging ends compatible with SstII and SfiI digested DNA, and having the following sequence:

***

5' GGACTGGCATCATGGCGCCCTCAGTTA-
CACTGCCGTTGACCACGGCCATCC 3'
3' CGCCTGACCGTAGTACCGCGGGAGT-
CAATGTGACGGCAACTGGTGCCGGT 5'

(SEQ ID NO: 4) The asterisks mark the translation initiation codon (ATG) of the egl1 gene coding region. The DNA sequence 5' to the ATG codon is exactly the same as that found in this region of the cbh1 gene. The DNA sequence 3' of the ATG codon is exactly the same as that found in this region of the egl1 gene.

d) An approximately 2 kb SfiI-ScaI fragment of *T. longibrachiatum* DNA containing the egl1 coding sequence, starting at an SfiI site 30 bp after the first ATG codon, and approximately 300 bp of 3' flanking DNA containing the transcription termination and polyadenylation signals.

e) An approximately 1 kb SmaI-BglII fragment of *T. longibrachiatum* DNA from the 3' flanking region of the cbh1 gene with a PmeI restriction site added adjacent to the SmaI site using the synthetic linker DNA shown in FIG. 9 (SEQ ID NO:1).

f) The *T. longibrachiatum* pyr4 gene on a 1.6 kb BglII fragment which has 13 bp on one end and 17 bp on the other end of synthetic linker DNA. Both linkers were derived from the multiple cloning site of the pUC219 vector. The latter synthetic linker was additionally modified by insertion of a BglII site at the HindIII site using the linker shown in FIG. 9 (SEQ ID NO:3). Oligonucleotide directed mutagenesis (Sambrook et al. (1989) Molecular Cloning a Laboratory Manual, Cold Spring Harbor Press) was used to change a single nucleotide within the pyr4 coding region (SEQ ID NO:2 of FIG. 9). The third nucleotide of the codon coding for the arginine residue at amino acid position 251 of the protein was changed from a C nucleotide to an A nucleotide by this method. This alteration would not change the amino acid sequence of the orotidine 5' monophosphate decarboxylase produced but destroyed an SstII site in the DNA sequence and thus facilitated construction of the plasmid.

g) An approximately 0.5 kb BglII-NheI fragment of *T. longibrachiatum* DNA from the 3' flanking region of the cbh1 gene.

It would be possible to construct plasmids similar to pTEX-EGI but with any other *T. longibrachiatum* gene replacing the egl1 gene. In this way, over-expression of other genes and simultaneous deletion of the cbh1 gene could be achieved.

EXAMPLE 14

Construction of EG I over-expression strains

The linear fragment of DNA containing the egl1 and pyr4 genes released from pEGIpyr4 by digestion with HindIII, was purified from an agarose gel. Similarly, the linear fragment of DNA containing the egl1, pyr4 genes and flanking regions of the cbh1 gene was purified from pTEX-EGI after digestion with NotI and NheI. These fragments of DNA were used in separate experiments to transform *T. longibrachiatum* strain P37PΔΔCBH67Pyr⁻1 by the method of Examples 3 and 4. Several transformants were obtained with each DNA fragment which transformants produced elevated levels of EGI compared to the parent strain. Total DNA was isolated from these transformants, digested with PstI, subjected to agarose gel electrophoresis and blotted to a membrane filter. Southern blot analysis using radiolabelled pUCEGI (a pUC plasmid containing the egl1 gene on a 4.2 kb HindIII fragment of genomic DNA) showed that each transformant contained multiple copies of the egl1 gene integrated at sites within the genome which could not be determined.

Similar Southern analysis was also performed using a pUC vector as a probe. This analysis revealed that the pUC plasmid fragment of either pEGIpyr4 or pTEX-EGI had not been incorporated by any of these strains.

Transformants of strain P37PΔΔCBH67Pyr⁻1 obtained with either pEGIpyr4 or pTEX-EGI as described above were inoculated into 50 ml shake flask cultures in order to determine the amount of secreted endoglucanase produced. The liquid medium used for these experiments had the following composition: alpha-lactose, 30 g/l; $(NH_4)_2SO_4$, 6.5 g/l; $KH_2PO_4$, 2.0 g/l; $MgSO_4.7H_2O$, 0.3 g/l; $CaCl_2$, 0.2 g/l; 1000×trace salt solution, 1.0 ml/l; 10 % Tween 80, 2.0 ml/l; Proflo, 22.5 g/l; $CaCO_3$, 0.72 g/l. Source for Tween 80 and Proflo. The 1000×trace salt solution had the following composition: $FeSO_4.7H_2O$, 5.0 g/l; $MnSO_4.H_2O$, 1.6 g/l; $ZnSO_4$, 1.4 g/l. These shake flask cultures were incubated with shaking for seven days at 30° C. Samples of the supernatant were taken from these cultures and assays designed to measure the endoglucanase activity were performed as described below.

The endoglucanase assay relied on the release of soluble, dyed oligosaccharides from Remazol Brilliant Blue-carboxymethylcellulose (RBB-CMC, obtained from MegaZyme, North Rocks, NSW, Australia). The substrate was prepared by adding 2 g of dry RBB-CMC to 80 ml of just boiled deionized water with vigorous stirring. When cooled to room temperature, 5 ml of 2 M sodium acetate buffer (pH 4.8) was added and the pH adjusted to 4.5. The volume was finally adjusted to 100 ml with deionized water and sodium azide added to a final concentration of 0.02%. Aliquots of *T. longibrachiatum* control culture, pEGIpyr4 or pTEX-EGI₁ transformant culture supernatants or 0.1 M sodium acetate as a blank (10–20 μl) were placed in tubes, 250 μl of substrate was added and the tubes were incubated for 30 minutes at 37° C. The tubes were placed on ice for 10 minutes and 1 ml of cold precipitant (3.3% sodium acetate, 0.4% zinc acetate, pH 5 with HCl, 76% ethanol) was then added. The tubes were vortexed and allowed to sit for five minutes before centrifuging for three minutes at approximately 13,000×g. The optical density was measured spectrophotometrically at a wavelength of 590–600 nm.

The results of the endoglucanase assay performed on triplicate cultures of 5 different transformants obtained with pEGIpyr4 DNA and on cultures of the parental strain P37PΔΔCBH67 are given in Table 1 below. It is apparent that the transformants produced significantly more secreted endoglucanase activity compared to the parental strain described above, are shown in Table 1.

TABLE 1

Secreted Endoglucanase Activity of *T. longibrachiatum* Transformants

| TRANSFORMANT | RBB-CMC UNITS/ML | | | | |
| --- | --- | --- | --- | --- | --- |
| | FLASK 1 | FLASK 2 | FLASK 3 | FLASK 4 | AVERAGE |
| P37 EP1 | 5.7 | 14.3 | 14.1 | | 11.4 |
| P37 EP8 | 11.0 | 3.8 | 6.1 | | 7.0 |
| P37 EP9 | 3.4 | 11.5 | 14.9 | | 9.9 |
| P37 EP10 | 7.0 | 9.1 | 5.0 | | 7.0 |

TABLE 1-continued

Secreted Endoglucanase Activity of
T. longibrachiatum Transformants

| TRANSFORMANT | RBB-CMC UNITS/ML | | | | |
|---|---|---|---|---|---|
| | FLASK 1 | FLASK 2 | FLASK 3 | FLASK 4 | AVERAGE |
| P37 EP11 parental | 5.0 | 5.5 | 10.0 | | 6.9 |
| P37PΔΔCBH67 | 3.0 | 2.8 | 5.5 | 1.1 | 3.1 |

The above results are presented for the purpose of demonstrating the overproduction of the EGI component and not for the purpose of demonstrating the extent of overproduction. In this regard, the extent of overproduction is expected to vary with each experiment.

Similar shake flask cultures and endoglucanase assays were performed with transformants obtained With pTEX-EGI and those transformants which overproduced endoglucanase activity were identified.

The methods of this example could be used to produce T. longibrachiatum strains which would overproduce any of the other EG components.

It would also be possible to transform pyr4 derivative strains of T. longibrachiatum which had previously been deleted for other genes in addition to CBHI and CBHII, e.g. for EGII, with pEGIpyr4 or pTEX-EGI to construct transformants which would, for example, produce no exocellobiohydrolases or EGII and overexpress EGI.

EXAMPLE 15
Purification of Cytolase 123 Cellulase
into Cellulase Components
CYTOLASE 123 cellulase was fractionated in the
following manner. The normal distribution of
cellulase components in this cellulase system is as
follows:

| CBH I | 45–55 weight percent |
| CBH II | 13–15 weight percent |
| EG I | 11–13 weight percent |
| EG II | 8–10 weight percent |
| EG III | 1–4 weight percent |
| BG | 0.5–1 weight percent. |

The fractionation was done using columns containing the following resins: Sephadex G-25 gel filtration resin from Sigma Chemical Company (St. Louis, Mo.), QA Trisacryl M anion exchange resin and SP Trisacryl M cation exchange resin from IBF Biotechnics (Savage, Md.). CYTOLASE 123 cellulase, 0.5 g, was desalted using a column of 3 liters of Sephadex G-25 gel filtration resin with 10 mM sodium phosphate buffer at pH 6.8. The desalted solution, was then loaded onto a column of 20 ml of QA Trisacryl M anion exchange resin. The fraction bound on this column contained CBH I and EG I. These components were separated by gradient elution using an aqueous gradient containing from 0 to about 500 mM sodium chloride. The fraction not bound on this column contained CBH II and EG II. These fractions were desalted using a column of Sephadex G-25 gel filtration resin equilibrated with 10 mM sodium citrate, pH 3.3. This solution, 200 ml, was then loaded onto a column of 20 ml of SP Trisacryl M cation exchange resin. CBH II and EG II were eluted separately using an aqueous gradient containing from 0 to about 200 mM sodium chloride.

Following procedures similar to that of Example 13 above, other cellulase systems which can be separated into their components include CELLUCAST (available from Novo Industry, Copenhagen, Denmark), RAPIDASE (available from Gist Brocades, N.V., Delft, Holland), and cellulase systems derived from Trichoderma koningii, Penicillum sp. and the like.

EXAMPLE 16

Purification of EG III from Cytolase 123 Cellulase

Example 22 above demonstrated the isolation of several components from Cytolase 123 Cellulase. However, because EG III is present in very small quantities in Cytolase 123 Cellulase, the following procedures were employed to isolate this component. See also U.S. Ser. No. 07/862,846 filed Apr. 3, 1992 and entitled "METHODS FOR PRODUCING SUBSTANTIALLY PURE EG III CELLULASE USING POLYETHYLENE GLYCOL", which is incorporated herein in its entirety by reference.

A. Large Scale Extraction of EG III Cellulase Enzyme

One hundred liters of cell free cellulase filtrate were heated to about 30° C. The heated material was made about 4% wt/vol PEG 8000 (polyethylene glycol, MW of about 8000) and about 10% wt/vol anhydrous sodium sulfate. The mixture formed a two phase liquid mixture. The phases were separated using an SA-1 disk stack centrifuge. The phases were analyzed using silver staining isoelectric focusing gels. Separation was obtained for EG III and xylanase. The recovered composition contained about 20 to 50 weight percent of EG III.

Regarding the above procedure, use of a polyethylene glycol having a molecular weight of less than about 8000 gave inadequate separation; whereas, use of polyethylene glycol having a molecular weight of greater than about 8000 resulted in the exclusion of desired enzymes in the recovered composition. With regard to the amount of sodium sulfate, sodium sulfate levels greater than about 10% wt/vol caused precipitation problems; whereas, sodium sulfate levels less than about 10% wt/vol gave poor separation or the solution remained in a single phase.

Alternatively, EG III cellulase may be extracted by the method described in U.S. Ser. No. 07/862,641 filed Apr. 3, 1992 which is entitled "METHODS FOR PRODUCING SUBSTANTIALLY PURE EG III CELLULASE USING ALCOHOL," which reference is incorporated herein in its entirety.

B. Purification of EG III Via Fractionation

The purification of EG III is conducted by fractionation from a complete fungal cellulase composition (CYTOLASE 123 cellulase, commercially available from Genencor International, South San Francisco, Calif.) which is produced by wild type *Trichoderma longibrachiatum*. Specifically, the fractionation is done using columns containing the following resins: Sephadex G-25 gel filtration resin from Sigma Chemical Company (St. Louis, Mo.), QA Trisacryl M ation exchange resin and SP Trisacryl M cation exchange resin from IBF Biotechnics (Savage, Maryland). CYTOLASE 123 cellulase, 0.5g, is desalted using a column of 3 liters of Sephadex G-25 gel filtration resin with 10 mM sodium phosphate buffer at pH 6.8. The desalted solution, is then loaded onto a column of 20 ml of QA Trisacryl M anion exchange resin. The fraction bound on this column contained CBH I and EG I. The fraction not bound on this column contains CBH II, EG II and EG III. These fractions are desalted using a column of Sephadex G-25 gel filtration resin equilibrated with 10 mM sodium citrate, pH 4.5. This solution, 200 ml, is then loaded onto a column of 20 ml of SP Trisacryl M cation exchange resin. The EG III was eluted with 100 mL of an aqueous solution of 200 mM sodium chloride.

In order to enhance the efficiency of the isolation of EG III, it may be desirable to employ *Trichoderma longibrachiatum* genetically modified so as to be incapable of producing one or more of EG I, EG II, CBH I and/or CBH II. The absence of one or more of such components will necessarily lead to more efficient isolation of EG III.

Likewise, it may be desirable for the EG III compositions described above to be further purified to provide for substantially pure EG III compositions, i.e., compositions containing EG III at greater than about 80 weight percent of protein. For example, such a substantially pure EG III protein can be obtained by utilizing material obtained from procedure A in procedure B or vice versa. One particular method for further purifying EG III is by further fractionation of an EG III sample obtained in part b) of this Example 14. The further fraction was done on a FPLC system using a Mono-S-HR 5/5 column (available from Pharmacia LKB Biotechnology, Piscataway, N.J.). The FPLC system consists of a liquid chromatography controller, 2 pumps, a dual path monitor, a fraction collector and a chart recorder (all of which are available from Pharmacia LKB Biotechnology, Piscataway, N.J.). The fractionation was conducted by desalting 5 ml of the EG III sample prepared in part b) of this Example 14 with a 20 ml Sephadex G-25 column which had been previously equilibrated with 10 mM sodium citrate pH 4. The column was then eluted with 0–200 mM aqueous gradient of NaCl at a rate of 0.5 ml/minute with samples collected in 1 ml fractions. EG III was recovered in fractions 10 and 11 and was determined to be greater than 90% pure by SDS gel electrophoresis. EG III of this purity is suitable for determining the N-terminal amino acid sequence by known techniques.

Substantially pure EG III as well as EG I and EG II components purified in Example 16 above can be used singularly or in mixtures in the methods of this invention. These EG components have the following characteristics:

| | MW | pI | pH optimum[1] |
|---|---|---|---|
| EG I | ~47–49 kD | 4.7 | ~5 |
| EG II | ~35 kD | 5.5 | ~5 |
| EG III | ~25–28 kD | 7.4 | ~5.5–6.0 |

[1]pH optimum determined by RBB-CMC activity as per Example 17 below.

EXAMPLE 17

Activity of Cellulase Compositions Over a pH Range

The following procedure was employed to determine the pH profiles of two different cellulase compositions. The first cellulase composition was a CBH I and II deleted cellulase composition prepared from *Trichoderma longibrachiatum* genetically modified in a manner similar to that described above so as to be unable to produce CBH I and CBH II components. Insofar as this cellulase composition does not contain CBH I and CBH II which generally comprise from about 58 to 70 percent of a cellulase composition derived from *Trichoderma longibrachiatum*, this cellulase composition is necessarily substantially free of CBH I type and CBH II type cellulase components and accordingly, is enriched in EG components, i.e., EG I, EG II, EG III, and the like.

The second cellulase composition was an approximately 20 to 40% pure fraction of EG III isolated from a cellulase composition derived from *Trichoderma longibrachiatum* via purification methods similar to part b) of Example 16.

The activity of these cellulase compositions was determined at 40° C. and the determinations were made using the following procedures.

Add 5 to 20 µl of an appropriate enzyme solution at a concentration sufficient to provide the requisite amount of enzyme in the final solution. Add 250 µl of 2 weight percent RBB-CMC (Remazol Brilliant Blue R-Carboxymethylcellulose—commercially available from MegaZyme, 6 Altona Place, North Rocks, N.S.W. 2151, Australia) in 0.05M citrate/phosphate buffer at pH 4, 5, 5.5, 6, 6.5, 7, 7.5 and 8.

Vortex and incubate at 40° C. for 30 minutes. Chill in an ice bath for 5 to 10 minutes. Add 1000 µl of methyl cellosolve containing 0.3M sodium acetate and 0.02M zinc acetate. Vortex and let sit for 5–10 minutes. Centrifuge and pour supernatant into cuvets. Measure the optical density (OD) of the solution in each cuvet at 590 nm. Higher levels of optical density correspond to higher levels of enzyme activity.

The results of this analysis are set forth in FIG. 10 which illustrates the relative activity of the CBH I and II deleted cellulase composition compared to the EG III cellulase composition. From this figure, it is seen that the cellulase composition deleted in CBH I and CBH II possesses optimum cellulolytic activity against RBB-CMC at near pH 5.5 and has some activity at alkaline pHs, i.e., at pHs from above 7 to 8. On the other hand, the cellulase composition enriched in EG III possesses optimum cellulolytic activity at pH 5.5–6 and possesses significant activity at alkaline pHs.

From the above example, one skilled in the art would merely need to adjust and maintain the pH of the aqueous textile composition so that the cellulase composition is active and preferably, possesses optimum activity. As noted above, such adjustments and maintenance may involve the use of a suitable buffer.

EXAMPLE 18

Stonewashed Appearance

This example demonstrates that the presence of CBH type components is not essential for imparting a stonewashed appearance to denim fabrics. Specifically, this example employs a cellulase composition derived from *Trichoderma longibrachiatum* genetically engineered in the manner described above so as to be incapable of producing any CBH type components (i.e., incapable of producing CBH I and II components) as well as a complete cellulase composition derived from *Trichoderma longibrachiatum* and which is available as Cytolase 123 cellulase from Genencor International, South San Francisco, Calif.

These cellulase compositions were tested for their ability to impart a stonewashed appearance to dyed denim denims pants. Specifically, the samples were prepared using an industrial washer and dryer under the following conditions:

10 mM citrate/phosphate buffer pH 5

40 L total volume

110° F.

Four pair of denim pants 1 hour run time 50 ppm CBH I and II deleted cellulase or 100 ppm whole cellulase (i.e., at approximately equal EG concentrations)

Samples were evaluated for their stonewashed appearance, but not the level of redeposition of dye, by 8 panelists. All eight panelists choose 100 ppm whole cellulase over non-enzyme treated pants as having the better stonewashed look. Four of the 8 panelists choose the CBH I and II deleted cellulase treated pants over whole cellulase as having the better stonewashed look; whereas the other four panelists choose the whole cellulase treated pants as having the better stonewashed look. These results indicate that the CBH I and II deleted cellulase treated pants were indistinguishable from whole cellulase treated pants and that CBH I and/or CBH II are not essential for imparting a stonewashed appearance to denim fabrics.

EXAMPLE 19

Reduced Redeposition of dye

This example demonstrates that the use of EG type components substantially free of CBH type components results in a reduced redeposition of dye onto the fabric during stonewashing.

Specifically, this example employs the following cellulase compositions:

a) a complete cellulase composition derived from *Trichoderma longibrachiatum* and which is available as Cytolase 123 cellulase from Genencor International, South San Francisco, Calif.

b) a cellulase composition from *Trichoderma longibrachiatum* genetically engineered in the manner described above so as to be incapable of producing any CBH type components (i.e., incapable of producing CBH I and II components);

c) CBH I purified by the method of Example 15;

d) EG I purified by the method of Example 15;

e) EG II purified by the method of Example 15; and f) EG III purified by the method of Example 16.

These cellulase compositions were tested for their ability to impart a stonewashed appearance to dyed denim pants and their ability to prevent the redeposition of dye onto the fabric.

Specifically, the samples were prepared using an industrial washer and dryer under the following conditions:

20 mM citrate/phosphate buffer pH 4.9

40 L total volume

55° C.

3.8 kg of desized indigo dyed denim pants 1 hour run time at 36 rpms 35 ppm CBH I and II deleted cellulase or 70 ppm whole cellulase or 15–30 ppm of purified EGI, EGII or EGIII cellulase The garments were rinsed according to a standardized protocol in three consecutive cycles of clean liquor. Rinse #1—24 gallons hot water, approximately 50° C., plus ~100 grams standard detergent WOR (from American Association of Textile Chemists and Colorists [AATCC], WOB— without brighteners). Agitation was for 12 minutes at 36 rpms. The bath was dropped. Rinse #2—24 gallons warm water, ~40° C., with no additional detergents, agitated for 5 minutes. The bath was dropped. Rinse #3—24 gallons cold water, ~30° C., with no additional detergents, agitated for 5 minutes. The bath was dropped. Garments were extracted and dried in a standard electric clothes dryer.

FIG. 11 shows that results obtained with the different cellulase compositions.

The results indicate that EG III gave the least redeposition of dye on the fabric. However, purified EG I, EG II and CBHI/II deleted cellulase also gave a satisfactory stonewashed appearance with less redeposition as compared to that obtained with whole cellulase. Although CBH I alone did not produce redeposition, it also did not generate a stonewashed effect.

The presence of substantial amounts of CBH type components in the cellulase composition appears to result in an increase in the redeposition of dye onto the fabric.

Cellulase compositions derived from microorganisms which produce redepositing whole cellulase compositions, other than *Trichoderma longibrachiatum*, that are substantially free of CBH type components could be used in place of the cellulase compositions described in this example. In particular, the source of the cellulase composition containing the EG type components is not important to this invention and any cellulase composition containing one or more EG type components and substantially free of all CBH-type components can be used herein. For example, fungal cellulases for use in preparing the fungal cellulase compositions used in this invention can be obtained from *Trichoderma viride, Trichoderma koningii,* Pencillium sp., and the like or commercially available cellulases can be used, i.e., CELLUCAST (available from Novo Industry, Copenhagen, Denmark), RAPIDASE (available from Gist Brocades, N.V., Delft, Holland), and the like.

What is claimed is:

1. A method for reducing colorant redeposition during stonewashing of colored fabrics said fabrics comprising colored threads alternating with white threads, by treatment of the fabric with a cellulase composition which method comprises contacting the fabric with an effective amount of a fungal cellulase composition substantially free of CBH type components and comprising at least about 40 weight percent of endoglucanase III derived from Trichoderma sp. which endoglucanase has a pH optimum of from about 5.0 to 7.0, an isoelectric point of about 7.2 to 8.0 and a molecular weight of from about 23 to 28 kDaltons wherein said contacting is conducted under conditions sufficient to impart a stone-washed appearance to the fabric while reducing the degree of colorant redeposition as compared to conventional stonewashing with Trichoderma sp. cellulase.

2. The method according to claim 1 further comprising contacting the denim with pumice stones.

3. The method according to claim 1 wherein said cellulase composition comprises at least about 80 weight percent of endoglucanase III derived from Trichoderma sp. based on the total weight of cellulase protein.

4. The method according to claim 1 wherein said cellulase composition further comprises a surfactant.

5. The method according to claim 1 wherein said cellulase composition further comprises a buffer.

6. The method according to claim 1 wherein said cellulase composition comprises a cellulase composition expressed by a Trichoderma sp. microorganism selected from the group consisting of *Trichoderma longibrachiatum* and *Trichoderma viride*.

7. The method according to claim 1 wherein said cellulase composition comprises a dry granular product.

8. The method according to claim 1 wherein said cellulase composition comprises an aqueous solution.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 22 base pairs
( B ) TYPE: nucleic acid
( C ) STRANDEDNESS: double
( D ) TOPOLOGY: linear (  x i  ) SEQUENCE DESCRIPTION: SEQ ID NO:1:

GGGGTTTAAA CCCGCGGGAA TT 22

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TGAGCCGAGG CCTCC 15

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:3:

AGCTTGAGAT CTGAAGCT 18

( 2 ) INFORMATION FOR SEQ ID NO:4:

( i ) SEQUENCE CHARACTERISTICS:
        ( A ) LENGTH: 53 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:4:

GCGGACTGGC ATCATGGCGC CCTCAGTTAC ACTGCCGTTG ACCACGGCCA TCC 53